US011406270B2

(12) United States Patent
Afzali-Ardakani et al.

(10) Patent No.: US 11,406,270 B2
(45) Date of Patent: *Aug. 9, 2022

(54) LAYERED AND MULTI-SECTIONAL PULSE WAVE SENSORS AND USE THEREOF

(71) Applicant: International Business Machines Corporation, Armonk, NY (US)

(72) Inventors: Ali Afzali-Ardakani, Ossining, NY (US); Kang-Wook Lee, Yorktown Heights, NY (US); Robert S. Olyha, Jr., LaGrange, IN (US)

(73) Assignee: International Business Machines Corporation, Armonk, NY (US)

( * ) Notice: Subject to any disclaimer, the term of this patent is extended or adjusted under 35 U.S.C. 154(b) by 728 days.

This patent is subject to a terminal disclaimer.

(21) Appl. No.: 15/855,045

(22) Filed: Dec. 27, 2017

(65) Prior Publication Data

US 2018/0116530 A1 May 3, 2018

Related U.S. Application Data

(62) Division of application No. 14/872,209, filed on Oct. 1, 2015, now Pat. No. 10,485,430.

(51) Int. Cl.
*A61B 5/02* (2006.01)
*A61B 5/0205* (2006.01)
(Continued)

(52) U.S. Cl.
CPC ........ *A61B 5/02055* (2013.01); *A61B 5/0002* (2013.01); *A61B 5/024* (2013.01);
(Continued)

(58) Field of Classification Search
CPC . A61B 5/02055; A61B 5/6843; A61B 5/7235; A61B 5/74; A61B 5/746;
(Continued)

(56) References Cited

U.S. PATENT DOCUMENTS 2,658,505 A 11/1953 Sheer
4,409,983 A 10/1983 Albert
(Continued)

FOREIGN PATENT DOCUMENTS

WO 2013165474 A1 11/2011

OTHER PUBLICATIONS

Arasanz Tena. "Double Optical Feedback Interferomety for biomedical applications." Master's Thesis, Escola Tencica Superior d'Enginyeria de Telecomunicacio de Barcelona (2013).
(Continued)

*Primary Examiner* — Christian Jang
(74) *Attorney, Agent, or Firm* — Harrington & Smith

(57) ABSTRACT

An apparatus includes a wearable sensor structure that includes multiple individual sensor units placed in a row. Each individual sensor unit includes a first portion to contact a surface of skin under which arteries and/or veins are to be located, and a second portion that contacts the first portion and is configured to have a capacitance. The first and second portions are configured to create a capacitance change in response to a squeezing or bending between the first portion and a fixed part of the second portion caused by a pulse pressure and release of the pulse pressure. The apparatus includes circuitry configured to measure waveforms for the individual sensor units. Each waveform captures the capacitance change for its corresponding individual sensor unit. The apparatus includes a wireless interface configured to transmit the waveforms. A computing system is also disclosed that analyzes the waveforms and can provide alerts based thereon.

7 Claims, 15 Drawing Sheets

(51) Int. Cl.
*A61B 5/00* (2006.01)
*A61B 5/021* (2006.01)
*A61B 5/024* (2006.01)
*A61B 5/117* (2016.01)

(52) U.S. Cl.
CPC ........ *A61B 5/0205* (2013.01); *A61B 5/02108* (2013.01); *A61B 5/681* (2013.01); *A61B 5/6822* (2013.01); *A61B 5/6843* (2013.01); *A61B 5/7235* (2013.01); *A61B 5/74* (2013.01); *A61B 5/746* (2013.01); *A61B 5/117* (2013.01); *A61B 5/4854* (2013.01); *A61B 5/7282* (2013.01); *A61B 2562/0247* (2013.01)

(58) Field of Classification Search
CPC . A61B 5/0002; A61B 5/0205; A61B 5/02108; A61B 5/024; A61B 5/6822; A61B 5/681; A61B 5/7282; A61B 5/117; A61B 5/4854; A61B 2562/0247
See application file for complete search history.

(56) References Cited

U.S. PATENT DOCUMENTS

| | | | |
|---|---|---|---|
| 6,491,747 B2 | 12/2002 | Bridger et al. | |
| 8,374,688 B2 | 2/2013 | Libbus et al. | |
| 10,485,430 B2 * | 11/2019 | Afzali-Ardakani | A61B 5/6843 |
| 2001/0011153 A1 * | 8/2001 | Bardy | A61B 5/0002 600/300 |
| 2006/0173712 A1 * | 8/2006 | Joubert | G16H 50/70 705/2 |
| 2006/0195035 A1 * | 8/2006 | Sun | A61B 5/02116 600/503 |
| 2008/0125288 A1 | 5/2008 | Case | |
| 2011/0208071 A1 * | 8/2011 | Lu | A61B 5/0285 600/500 |
| 2012/0253154 A1 | 10/2012 | Phillips | |
| 2014/0249424 A1 | 9/2014 | Fan et al. | |
| 2016/0051195 A1 * | 2/2016 | Pang | A61B 5/02055 600/301 |

OTHER PUBLICATIONS

Mannsfeld et al. "Highly sensitive flexible pressure sensors with microstructured rubber dielectric layers." Nature materials 9.10 (2010): 859-864.
Shyamkumar et al., "Wearable Wireless Cardiovascular Monitoring Using Textile-Based Nanosensor and Nanomaterial Systems", Electronics 2014, 3, 504-520; doi: 10.3390/electronics3030504, ISSN 2079-9292.
Choong et al., "Highly stretchable resistive pressure sensors using a conductive elastomeric composite on a micropyramid array." Advanced Materials 26.21 (2014): 3451-3458.
Zang, et al. "Advances of flexible pressure sensors toward artificial intelligence and health care applications." Materials Horizons (2015).
Tee et al., "Tunable Flexible Pressure Sensor Using Microstructured Elastomer Geometries for Intuitive Electronics", Adv. Func. Mater. 2014, 24, 5427-5434, www.MaterialViews.com.
Pang et al., "Highly Skin-Conformal Microhairy Sensor for Pulse Signal Amplification", Adv. Matter 2014, www.MaterialViews.com.
Crilly et al., "Indices of Cardiovascular Function Derived from Peripheral Pulse Wave Analysis Using Radial Applanation Tonometry a Measurement Repeatability Study", Vasc Med 2007 12:189.
Rai et al., "Nanotextile Bio-Sensors for Mobile Wireless Wearable Health Monitoring of Neurological and Cardiovascular Disorders", Institute of Smart Structures and Systems (ISSS), J. ISSS vol. 3, No. 1, pp. 28-77 Mar. 2014.

* cited by examiner

LAYERED AND MULTI-SECTIONAL PULSE WAVE SENSORS AND USE THEREOF

CROSS-REFERENCE TO RELATED APPLICATIONS

This application is a divisional application of U.S. Ser. No. 14/872,209, filed on Oct. 1, 2015, the disclosure of which is hereby incorporated by reference in its entirety.

BACKGROUND

This invention relates generally to sensors and, more specifically, relates to wearable pulse wave sensors.

Abbreviations used in the specification and/or drawings are defined below, prior to the claims.

Cardiovascular diseases (CVDs) are the first cause of death worldwide. According to a World Health Organization (WHO) report, about 17.3 million people died because of CVDs in 2008, accounting for 30 percent of total global deaths, and the number is expected to rise to 23 million in 2030. See the World Health Organization's web page for cardiovascular diseases (2013). However, many of these deaths can be avoided by early diagnosis and reasonable care.

There are different sensors that may be used to detect CVDs. Recently, there has been more emphasis lately on wearable and flexible sensors. Any wearable sensor that is useful to prevent or detect CVDs or other conditions in real time is beneficial.

SUMMARY

The following summary is merely intended to be exemplary. The summary is not intended to limit the scope of the claims.

In one aspect, an apparatus is disclosed that includes a sensor structure. The sensor structure includes a plurality of individual sensor units placed in a row. Each individual sensor unit comprises a first portion configured to contact a surface of skin under which arteries or veins or both are to be located, and a second portion that contacts the first portion and is configured to have a capacitance. The first and second portions are configured to create a capacitance change in response to a squeezing or bending between the first portion and a fixed part of the second portion caused by a pulse pressure under the skin and in response to a return to an original state of the first portion with a release of the pulse pressure. The apparatus also includes circuitry connected to the sensor structure and configured to measure waveforms for the plurality of individual sensor units and configured to digitize the measured waveforms, wherein each waveform captures the capacitance change for its corresponding individual sensor unit. The apparatus also includes a wireless interface, the wireless interface configured to transmit the digitized measured waveforms.

In another aspect a computer-implemented method is disclosed that performs data analysis on multiple sets of data. Each set comprises previously measured waveforms for a plurality of individual sensor units placed in a row and responsive to pulse pressure under the skin. Each previously measured waveform captures capacitance change caused by the pulse pressure for its corresponding individual sensor unit. The method includes correlating the multiple sets of data to determine an outcome.

DETAILED DESCRIPTION

The word "exemplary" is used herein to mean "serving as an example, instance, or illustration." Any embodiment described herein as "exemplary" is not necessarily to be construed as preferred or advantageous over other embodiments. All of the embodiments described in this Detailed Description are exemplary embodiments provided to enable persons skilled in the art to make or use the invention and not to limit the scope of the invention which is defined by the claims.

For ease of reference, the instant disclosure is divided into sections.

1. Introduction

As described above, according to WHO, CVDs are the first cause of death worldwide. Arterial pulse wave analysis has been used to provide useful information regarding the mechanical properties of the arterial tree. Its assessment is an important tool in hypertension evaluation and cardiovascular prevention and risk stratification. See, e.g., the following: A. Avolio, M. Butlin and A. Walsh, "Arterial blood pressure measurement and pulse wave analysis—their role in enhancing cardiovascular assessment," Physiol. Meas. 2010, 31, R1-R47; and M. Crilly, C. Coch, M. Bruce, H. Clark and D. Williams, "Indices of cardiovascular function derived from peripheral pulse wave analysis using radial applanation tonometry: a measurement repeatability study," Vascular Medicine 2007, 12 (3), 189-197. Early detection and alarm of a stroke's onset are pivotal for improving current stroke's management.

On the other hand, wearable health-monitoring systems (WHMS) have drawn a lot of attention from the research community and the industry during the last decade. See, e.g., the following: A. Pantelopoulos and N. G. Bourbakis, "A Survey on Wearable Sensor-Based Systems for Health Monitoring and Prognosis," IEEE Trans. Sys. Man and Cyber. 2010, 40 (1), 1-12; and P. Shyamkumar et al., "Wearable Wireless Cardiovascular Monitoring Using Textile-Based Nanosensor and Nanomaterial Systems," Electronics 2014, 3, 504-520. Wearable pulse wave detection devices can be used for in-patients and out-patients as well as elderly or high-risk persons, e.g., as pulse wave monitoring and alarming systems. See Y. Yang, "Continuously wearable non-invasive apparatus for detecting abnormal health conditions," US Patent WO2013165474 A1 (2013). The sensitivity of pulse wave sensors has improved a lot recently by using combination of air and pyramid-shape dielectric (B. C.-K. Tee et al., "Tunable Flexible Pressure Sensors using Microstructured Elastomer Geometries for Intuitive Electronics," Adv. Funct. Mater. 2014, 24, 5427-5434) as well as by employing skin-conformal microhairy layers (see C. Pang, et al., "Highly Skin-Conformal Microhairy Sensor for Pulse Signal Amplification," Adv. Mater. 2014).

Figure 1:
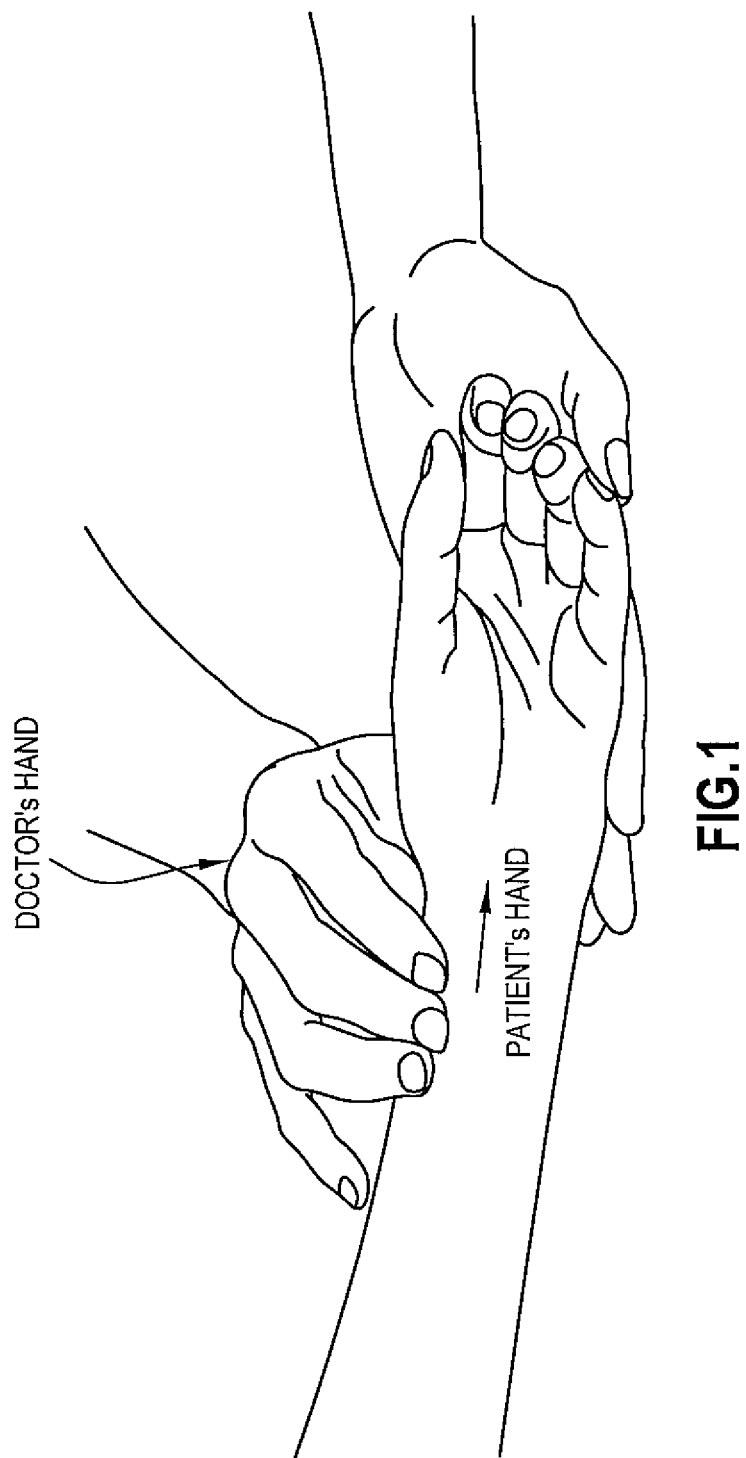
FIG. 1 illustrates diagnosis of wrist pulses with three fingers in oriental medicine.

In oriental medicine practiced for thousands of years, the arterial pulses of a patient have been examined by a doctor by placing the doctor's index, middle and ring fingers onto the patient's right or left wrist as shown in FIG. 1. The three fingers can touch a wrist gently or press a little hard so as to feel the pulse beatings. The pulse properties from each finger supposedly correspond to the normality or abnormality of two different organs as one organ from a gentle touch and the other from a hard press. Thus, a well-trained doctor can supposedly diagnose the states of up to 12 different organs including the heart, kidney, intestines, lungs, colon, stomach, pancreas, womb, and bladders. For example, a doctor places his or her index, middle and ring fingers, in order from the hand side. The beatings felt on the index finger when gently touched on the left wrist correspond to the heart while those when pressed hard on the same left wrist correspond to the intestines. Regular and mild beatings which are called "normal sinus rhythm" indicate healthy organs while irregular, too weak or too strong beatings which are called "arrhythmia" point out an abnormal state of the organ. A certain abnormal state can suggest a seriously poor state of the organ which is often related to a disease. See the following: Giovanni Maciocia, The Foundations of Chinese Medicine: A Comprehensive Text for Acupuncturists and Herbalists, 2nd Ed, 2005, Elsevier Churchill Livingstone, ISBN 0443074895; and Sean Walsh and Emma King, "Pulse Diagnosis: A Clinical Guide," 2007, Elsevier Health Sciences, ISBN 9780702047886.

As the sensitivity of pulse sensors keeps improving, the sensors can be used to diagnose CVDs as well as various diseases related to specific organs as practiced in oriental medicine. However, the relationships between digitized pulse data and organ states or diseases have not been studied or used.

Figure 2:
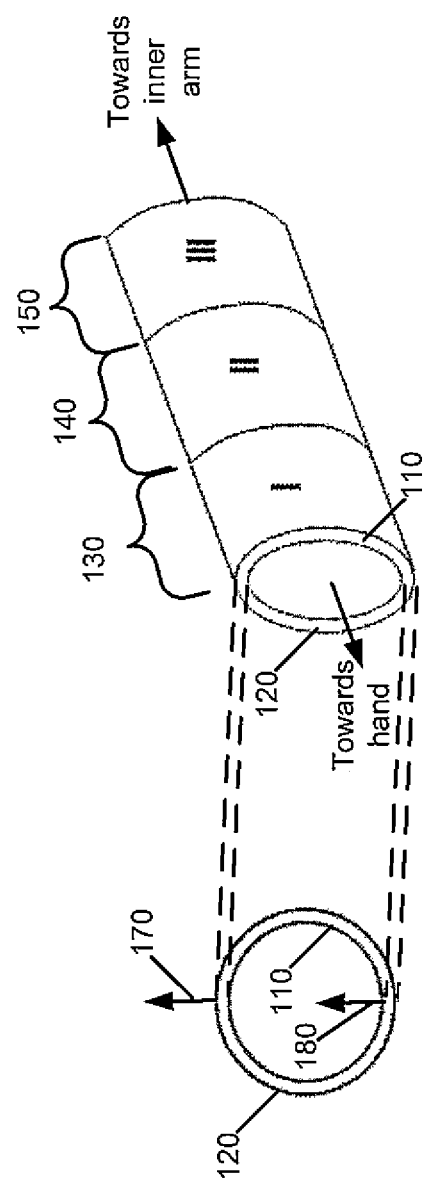
FIG. 2 is an illustration of double-layer, three-section sensors, which in an exemplary embodiment may be utilized to simulate the practice in oriental medicine illustrated by FIG. 1.

It is disclosed here that a pulse wave sensor device is designed to have layered and multi-section sensor units, for instance two layer and three sections 130, 140, and 150 as illustrated in the example of FIG. 2 and other figures herein. In this example, there are two layers, where the first layer is a skin touching portion 110 that contacts skin (illustrated by direction 180) and the second layer is a sensing portion 120 that connects to a wireless (or wired) device (illustrated by direction 170). In terms of the sections, section I (130) is close to the hand, while section II (140) is in the middle, and section III (150) is towards the inner arm.

2. Example 1

This section provides one example of an individual pulse wave sensor unit.

Figure 3:
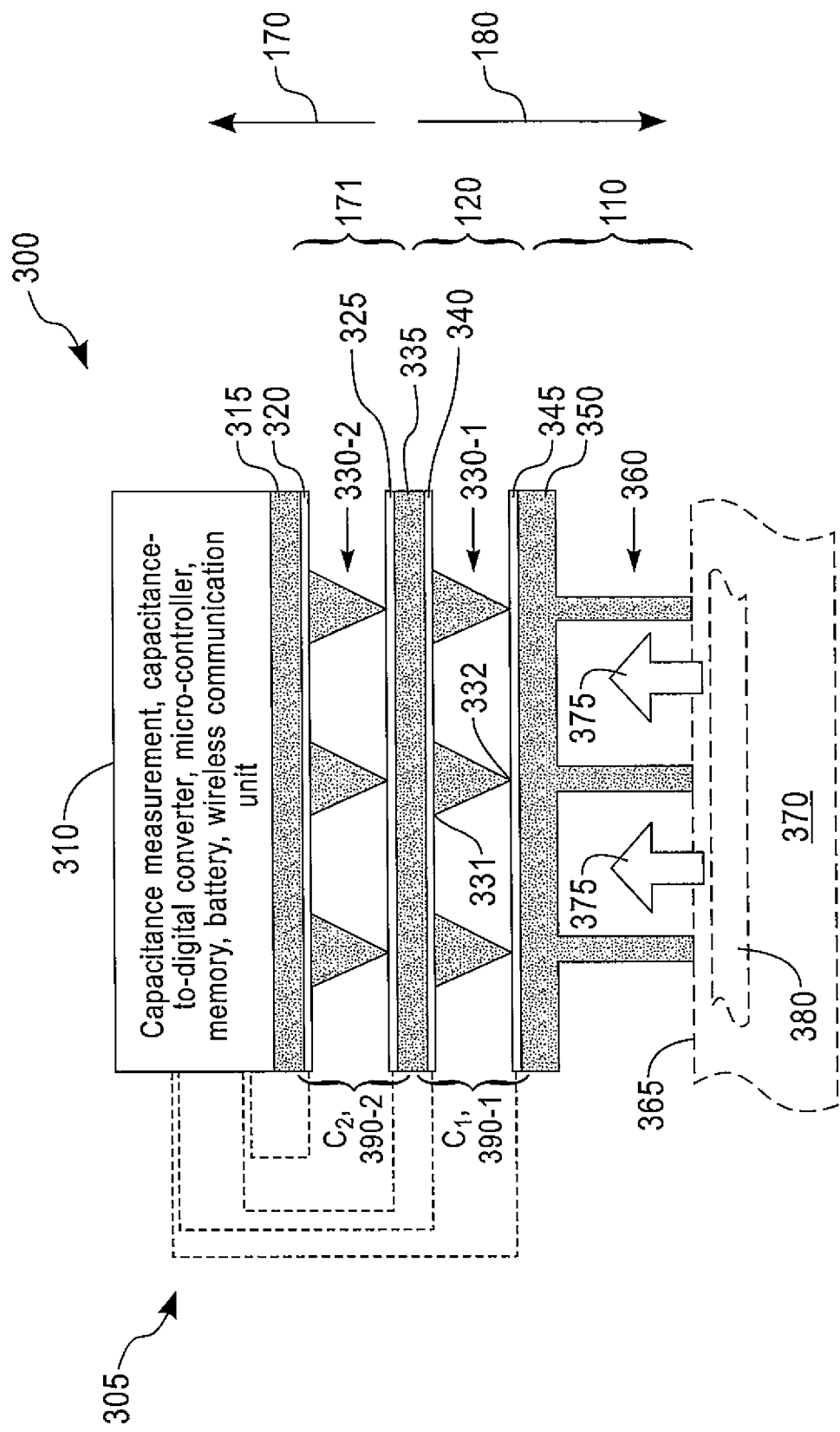
FIG. 3 illustrates a cross-section of an individual pulse wave sensor unit of a double-layered sensor.

The design of the pulse wave sensor unit, in one example, includes a dielectric layer and particularly pyramid-shaped elastomeric dielectrics to maximize the change of capacitance by the same pressure from arteries and the sensor also involves microhairs to enhance the contact of the sensor to skin so as to enhance the detection sensitivity as shown in FIG. 3. Individual pulse wave sensor unit 300 includes a first layer, a skin touching portion 110, and a second layer, sensing portion 120. Additionally, there is a third layer 171. The skin touching portion 110 comprises a dielectric layer 350 and dielectric microhairs 360. The sensing portion 120 comprises conductive (e.g., metal) layers 340 and 345, and dielectric pyramids 330-1. Each dielectric pyramid 330 has a base 331 and an apex 332. The conductive layers 340 and 345 and dielectric pyramids 330-1 and air in the gap form a capacitor $C_1$, 390-1. The third sensor layer 171 comprises conductive (e.g., metal) layers 320, 325 and dielectric pyramids 330-2. The conductive layers 320, 325 and dielectric pyramids 330-2 and air in the gap form a capacitor $C_2$, 390-2. In this example, the sensing portion 120 also includes a flexible polymer 335, although in other examples, the flexible polymer 335 may be assumed to divide the portions 110,120. Combination of the flexible polymers 315, 335 and 350 and the thin (30 nm-300 nm) conductive layers 320, 325, 340 and 345 provides a good flexibility of the overall sensor and thus the sensor can be wearable and flexible. The individual pulse wave sensor unit 300 also comprises a dielectric layer 315 onto which control circuitry 310 is attached. The control circuitry 310 includes, in this example, capacitance measurement circuitry, capacitance-to-digital converter circuitry, a micro-controller, a memory (e.g., to store a program for the micro-controller and to store digitized pulse wave(s)), a battery, and a wireless communication unit. Note that one or both of the capacitance measurement circuitry and/or the capacitance-to-digital converter may be implemented by the micro-controller. Additionally, the control circuitry 310 may use AC (alternating current) or other power source instead of or in addition to a battery. The various conductive layers 320, 325, 340, and 345 may be interconnected via the connectors 305 and the control circuitry 310. The connectors 305 may be wires, metal runs on a circuit board or integrated circuit, and the like.

In this example, the individual sensor unit 300 is shown contacting skin 365 of a body part 370, which contains one or more arteries 380 (of which one is shown in FIG. 3). The arteries 380 generate pulse pressures 375 that pass through the first and second portions 110, 120 (and the third sensor layer 171) and cause squeezing (e.g., deformation and bending) of the elastomeric pyramids of the first and second portions 110, 120 (and the third layer 171) at least to some extent. This squeezing therefore causes a capacitance change, and the circuitry 310 can determine waveforms capturing this change. Additionally, the first and second portions 110, 120 (and the third layer 171) are configured to create a capacitance change in response to a return of the portions to an original state with a release of the pulse pressure. It is assumed that at least the elements 315 and 320 are fixed (e.g., to a watch for instance) and the squeezing occurs between the elements 315/320 and the portions 110, 120, and part (e.g., elements 325, 330) of 171. It is desirable that the squeezing occurs mostly with the elastomeric pyramids so that the change of the capacitance between the two conductive layers 345 and 340 or 325 and 320 can be maximized.

In one example, the dielectric pyramids 330-1 and dielectric microhairs 360 are made of the same dielectric material. Alternatively, they may be different materials. The microhairs 360 provide good contact with the skin 365. That is, the microhairs 360 improve the contact to skin so as to enhance the detection sensitivity. Furthermore, one can adjust the elastomeric behavior to provide good contact with the skin. Assuming that PDMS is used, for instance, PDMS is made of a resin and a curing agent. For example, a mixture of 10:1 resin:curing agent provides a stiffer polymer when cured than a 5:1 mixture, as a smaller amount of curing agent gives a longer chain polymer. See, e.g., C. Pang, et al, "Highly Skin-Conformal Microhairy Sensor for Pulse Signal Amplification," Adv. Mater. 2014. In FIG. 3, the microhairs 360, dielectric pyramids 330-1, and dielectric pyramids 330-2 are illustrated as being aligned in the vertical dimension. This alignment is, however, not necessary and used solely for ease of illustration.

The shape of the dielectrics 330-1, 330-2 are exemplary, but use of pyramid shapes helps to increase the pulse wave signal to noise ratio so as to improve the data quality. The dielectric pyramids 330-1, 330-2 may be made of polymeric elastomer such as poly(dimethylsiloxane), PDMS. The two capacitors $C_1$, 390-1 and $C_2$, 390-2 are operated in series in an embodiment.

In terms of a two-dimensional array for the individual sensor unit 300, rows and columns of pyramids may be arranged with the same distances between pyramids in the x- or y-direction. The distance between pyramids can be, for instance, one to one hundred times of the pyramid base width. For instance, if the base width is 10 μm, the distance can be 10-1000 μm. The longer the distance between pyramids, the more sensitive the sensor. But the shorter distance would provide consistent pulse waves and also be more reliable in physical structure. Six pixels (that is, individual sensor units) can provide up to six waves in two dimensions.

3. Example Measurements and Results

Assuming there are six sensor units (referred to also as "pixels" herein), each of the six sensor units is wired, in one example, to each of six capacitance-measuring units in control circuitry 310. AC can be used for a continuous measurement, for instance, for in-hospital patients, while DC can be used for other users, such as out-patients or elderly persons, e.g., by turning the system on for only several minutes per day so as to minimize the power usage. The capacitance change is then digitized by the capacitance-to-digital converter circuitry. In an example, all digital data are wirelessly transmitted in an exemplary embodiment to, e.g., a computer server. The digitized waves can include heart rate, cardiac rhythm and pulse pattern as the signals of EKG (electrocardiogram) and the device can be used as an EKG so as to predict the onset of critical heart attacks, strokes, or errors in the autonomous nervous system.

Figure 4A:
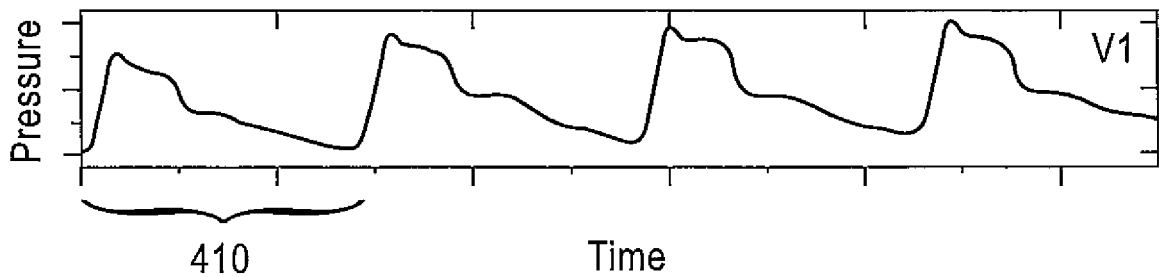
FIGS. 4A and 4B, collectively referred to herein as FIG. 4, are illustrations of pulse sinus waves and a single pulse sinus wave, respectively.
Figure 4B:
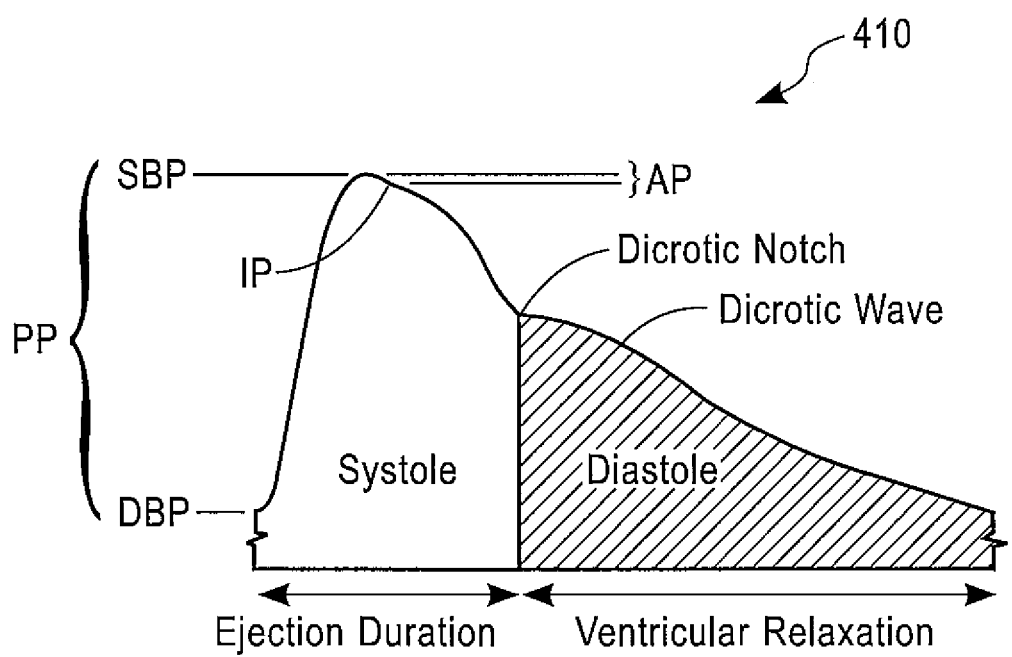

The digitized pulse sinus waves, as illustrated in FIG. 4, including both FIG. 4A and FIG. 4B, can be stored and then used to make pulse wave-disease relationships. FIG. 4A is an illustration of pulse sinus waves determined using the individual sensor unit 300. FIG. 4B is a single pulse sinus wave 410 from FIG. 4A. The single pulse wave 410 illustrates two portions of the wave, a systole portion having an ejection duration and a diastole portion having a ventricular relaxation duration. The systole portion illustrates the DBP (diastolic blood pressure), SBP (systolic blood pressure) points, along with the IP (inflection point). Between the two portions is the dicrotic notch, and the dicrotic wave forms the diastole portion. Cardiovascular pulse waves were systematically studied and reported by Z. Fan, et al. See Z. Fan, et al., "Pulse Wave Analysis" in "Adv. Biomedical Eng." Edited by G. D. Gargiulo and A. McEwan, pp. 21-40, on www.intechopen.com. 2011 and also Z. Fan, et al, US Patent Application number 2014/0249424.

The three-section pulse wave sensors may be used to set up a scientific relationship between diseases and sinus pulse waves so that a database can be created. In return, the accumulated "big data" will be used to diagnose a person with risk factors. Especially, an elderly person can wear a wireless sensor device for daily or hourly observations. Any abnormal behaviors may be detected by a server which subsequently warns the person as well as his or her doctor via, e.g., wireless systems in real time. Such devices will be very effective in diagnosing cardiovascular diseases. An advanced system with sensitive sensors and IT technology can protect human beings from sudden death or damage to at organ.

Figure 5A:
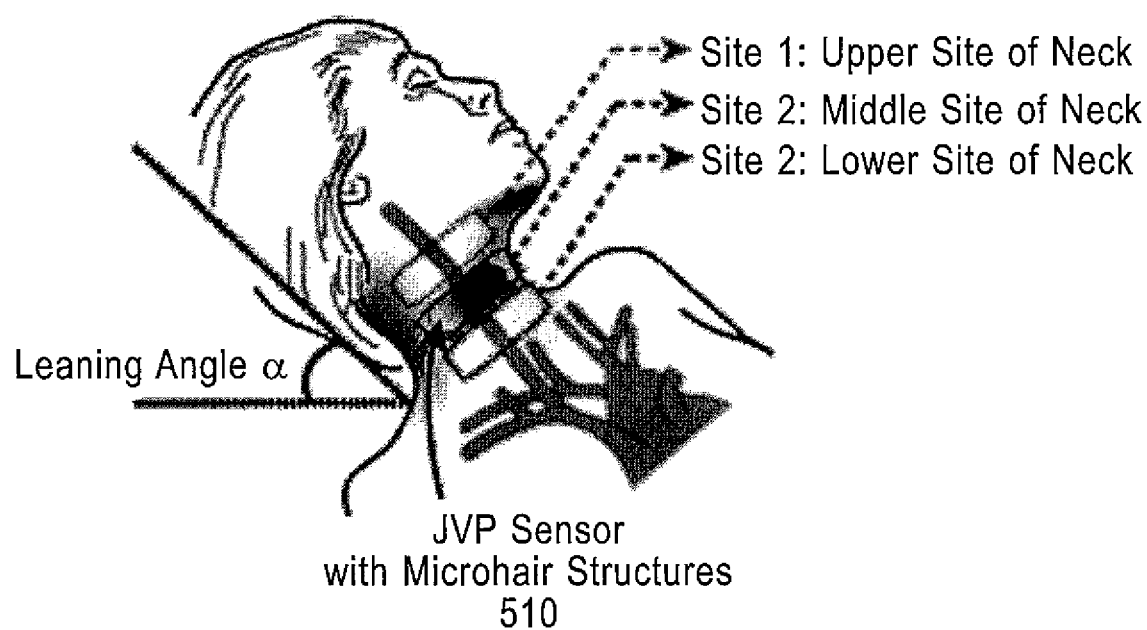
FIGS. 5A and 5B, collectively referred to herein as FIG. 5, are illustrations of a jugular venous pulse (JVP) sensor placed on a person and a typical JVP waveform, respectively.
Figure 5B:
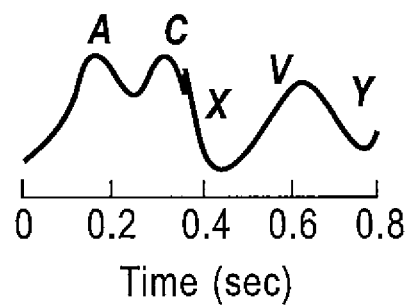

The sensors can also be used on other parts of human bodies such as the neck. Jugular venous pulses (JVPs) are known to be associated with arrhythmias, right heart hemodynamics, or pericardial disease. Pulse waves for internal JVPs can be measured by holding or using the device on the neck jugular vein surfaces as illustrated in FIG. 5. FIG. 5A is an illustration of a JVP sensor placed on a person and FIG. 5B is an illustration of a typical JVP waveform. These figures are from C. Pang, et al., "Highly Skin-Conformal Microhairy Sensor for Pulse Signal Amplification," Adv. Mater. 2014. Pulse rate and pressure can be easily monitored. Diagnosis of a sudden heart malfunction in a part of heart can be especially effective. Monitoring pulses such as JVPs can save lives. For example, a sensor attached to a person may transmit digitized JVPs to a server which in turn sends an alarm to a doctor, who can be ready for an immediate treatment upon arriving at a hospital or call the person to deliver an instruction to save her or his life.

In other embodiments, relationships between pulse waves and diet as well as the relationships between pulse waves and medicinal herbs can be established and used for health maintenance. Such relationships can be used to develop a specific diet or use of a medicinal herb for a person.

In other embodiments, relationships between pulse waves and a certain exercise can be established and used for health maintenance. Such relationships can be used to apply a specific exercise to prevent a disease, especially in case of family history or risk factors.

In another embodiment, each person can document his or her pulse waves. As a person gets older, changes of pulse waves can be diagnosed against a potential disease development so as to prevent or alert the person to the actual disease. The person can be connected, e.g., via a cloud system from any place in the world.

In another embodiment, temperature sensors are incorporated to the pulse sensors so that the device can recognize an appropriate contact to human skins (or another animal's skin). This the pulse sensors may turn on when properly touched onto a human skin. To avoid confusion between the human body temperature and the ambient temperature, the device may function only in a certain range of ambient temperature (for example, from zero degrees Celsius to 30 degrees Celsius).

In another embodiment, one sensor device has multiple pixels, the size of which ranges from, e.g., 25 mm$^2$ to 1000 mm$^2$. Each pixel can measure pulse waves independently. The relatively strong signals only from selected pixels can be used for a certain disease diagnosis. A semiconductor chip can be designed and manufactured to collect and wirelessly transmit the digitized pulse data. Such semiconductor chips and sensors can be included in a wearable sensor such as a smart watch. The smart watch can be wirelessly connected to a server, which identifies a problem using "big data" (e.g., many data sets from many different people) and then sends a warning to the patient wearing the watch, e.g., and also to a doctor. The doctor can electronically send an advice or a first aid to the patient.

4. Example 2

Figure 6A:
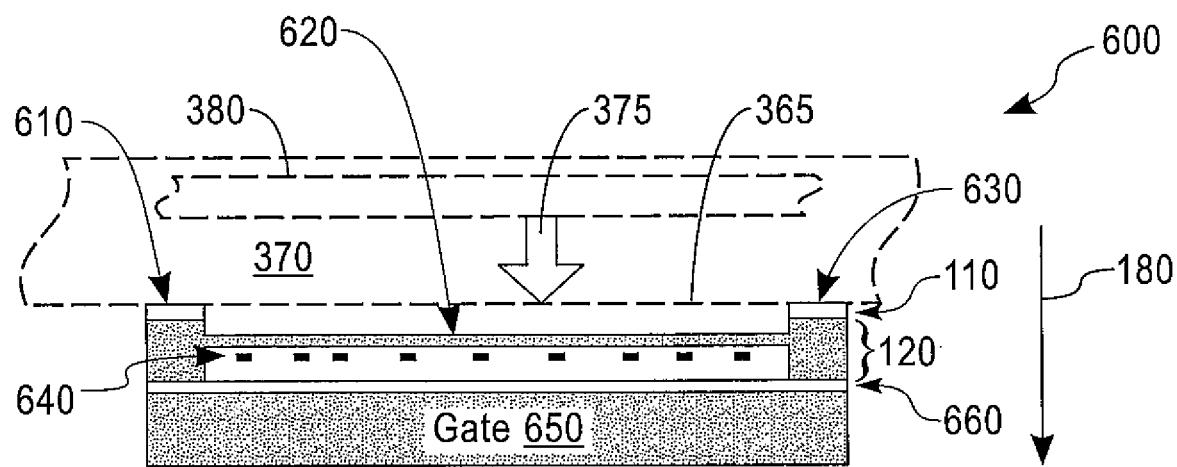
FIGS. 6A and 6B, collectively referred to herein as FIG. 6, are illustrations of an individual sensor unit before application of a pressure and the sensor unit after application of the pressure, respectively.
Figure 6B:
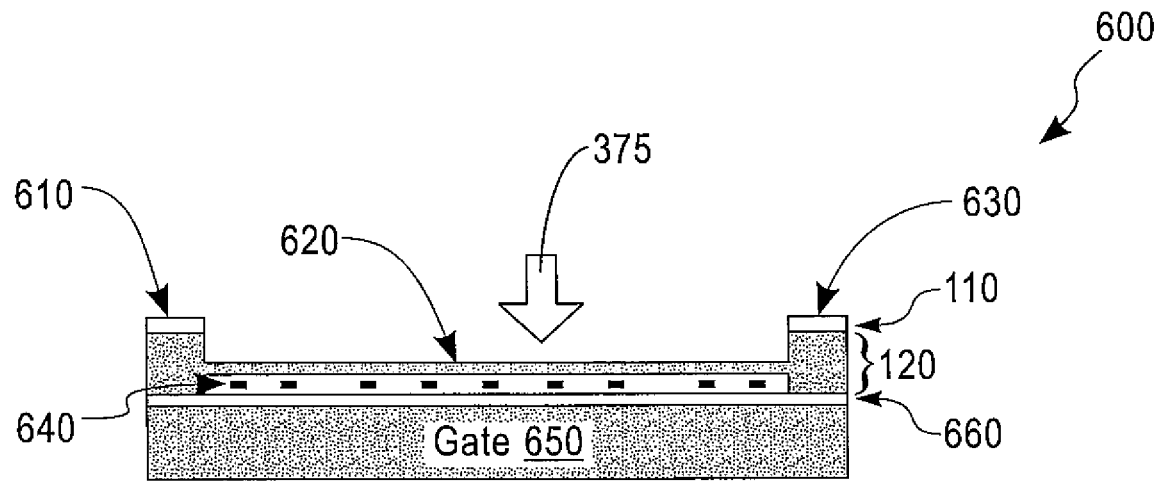

Turning to FIG. 6, this figure has FIG. 6A, which is an illustration of an individual sensor unit 600 before application of a pressure, and FIG. 6B, which is an illustration of the sensor unit 600 after application of the pressure. In FIG. 6, the individual sensor unit 600 comprises a drain 610, a source 630, a dielectric layer 660, and a gate 650, and this part of the unit 600 is similar to a field effect transistor (FET) in semiconductors. A skin touching portion 110 is to be in contact with the skin 365 of the body part 370. The skin touching portion 110 includes the nanowire 620, the source 630 and the drain 610. A nanowire 620 is suspended over the dielectric layer 660 and beneath the nanowire 620 are charged self-assembled monolayers (SAMs) 640. The sensing portion 120 comprises the SAMs 640 (e.g., in corresponding relationship to the nanowire 620). Application of pressure (e.g., by a pulse wave of the artery 380) bends (see FIG. 6B) the nanowire 620 and the charged SAMs 640 get closer to (or touch) the dielectric layer 660 and hence changes the capacitance of the dielectric layer between the source 630 and the gate 650.

Application of pressure is performed by the pulse pressure 375 (e.g., wave) in the artery 380 being applied to the nanowire 620. This causes a squeezing or bending of the nanowires 620, e.g., between the skin 365 and the dielectric 660. Additionally, the first and second portions 110, 120 are configured to create a capacitance change in response to a return of the nanowires 620 to an original state with a release of the pulse pressure. It is assumed the dielectric layer 660 and the gate 650 are fixed in position, e.g., via a wearable surface such as a watch or neckband. It is noted that the illustration in FIG. 6 makes it appear that the source 630 and drain 610 are above the level of the nanowires 620. However, the nanowires 620 would be in contact with the skin 365 of the body part 370 (which could be the wrist, neck, or other suitable body part).

More particularly, it is disclosed here that an individual sensor unit 600 is made of nanowires 620 coated (e.g., on all sides) with SAMs 640, which may be charged to enhance the sensitivity to pulse pressure changes. Each nanowire 620 is formed between drain 610 and source 630. Underneath each nanowire 620, a HfO$_2$ layer (as dielectric layer 660) and highly doped Si gate 650 are placed as illustrated in FIG. 6. Boron, arsenic, phosphorus, and gallium are used to dope silicon. Highly doped silicon acts more like a conductor than a semiconductor. The concentration of dopant atoms in highly doped silicon is in the order of 10E17 to 10E19 atoms/cubic centimeter, which correspond to a resistivity of 0.1 to 1.0 Ohm cm. The nanowires 620 are mostly silicon nanowire, although other III-V materials like indium-phosphide, gallium-arsenide, etc., could be used. Nanowires are fabricated by lithography and wet or dry etch. A capacitance change between the source 630 and the gate 650 is measured (in this case because the dielectric surface is not coated with charged monolayers and the nanowires are, and changing the distance between nanowires which are coated with charged monolayer and the dielectric 660 will change the capacitance of the dielectric). There are many different SAMs that may be used for this purpose. Typical SAMs are organic molecules. Examples are negatively charged carboxylates or positively charged pyridinium or positively charged ammonium salts, covalently attached to a silicon surface by reacting with corresponding diazonium salts.

When nanowires are not coated with charged SAMs 640, external pressure on nanowires causes bending of the nanowire 620, which results in changing of the conduction between source 630 and drain 610. When the nanowires 620 are coated with charged SAMs 640, bending of the nanowire 620 brings the charges closer to the surface of dielectric layer 660 (for example, HfO$_2$) which can be measured by changes in capacitance.

The longer the suspended nanowire 620, the more sensitive the pressure sensor. Also, the smaller the diameter of a nanowire, the more sensitive the sensor. But a longer and thinner nanowire can be mechanically less stable. Thus the length and diameter should be chosen appropriately. It is expected that the length may be 10-100 µm and the diameter may be 10-20 nm. One can arrange many arrays with different channel lengths and diameters in order to, e.g., increase or maximize the sensitivity. For example, the longest channel length should be placed at the lowest pressure area and the shortest at the highest pressure area. A sensor 600 can have multiple pixels, each of which can output a pulse wave. Each pixel can have 1-100 nanowires and thus the size of each pixel may vary.

A sensor 600 may be designed that one semiconductor device (such as control circuitry 310 of FIG. 3) is designed to measure the capacitance changes, to digitize the capacitance changes, and then to transmit the digitized data to a server system.

A wearable sensor device typically consists of multiple sensor units, while a sensor unit has multiple transistors, each of which is made of a nanowire, a source, a drain and highly-doped Si gate. Each sensor unit can output an independent pulse wave. Each sensor unit is wired to each of the capacitance-measuring units (e.g., in the case of one capacitance-measuring unit per sensor unit). It may be possible also for one capacitance-measuring unit to be shared between multiple sensor units, e.g., by time multiplexing measurements to the capacitance-measuring unit, for the example of FIG. 6 and the other examples herein. The capacitance change is then digitized. All digital data may be (e.g., wirelessly) transmitted to a computer server.

5. Additional Variations and Use of the Sensors

Figure 7A:
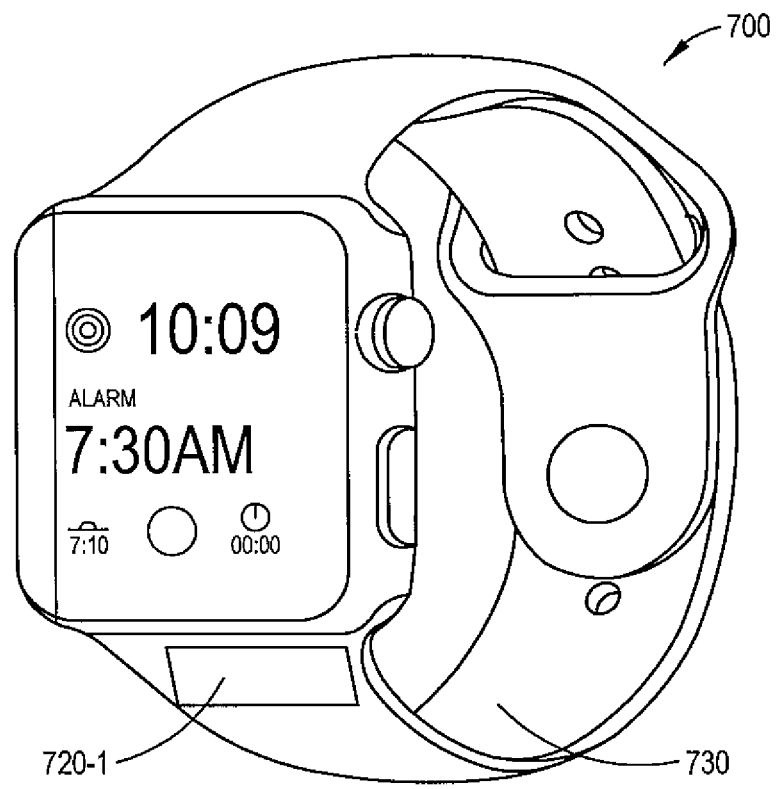
FIG. 7A illustrates a possible wearable device for carrying embedded sensors.
Figure 7B:
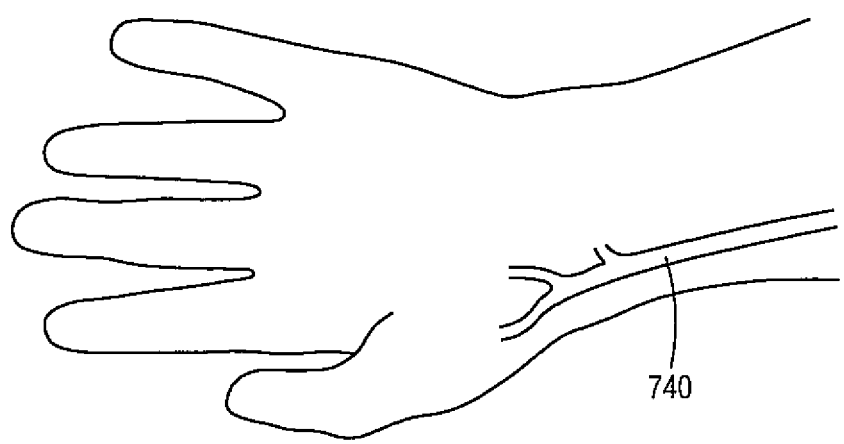
FIG. 7B illustrates a possible location on a body where the wearable device of FIG. 7A might be used.

This section describes additional variations using sensors for layered and multi-sectional pulse wave sensors and use of the sensors. Turning to FIG. 7A, this figure illustrates a possible wearable device 700 for carrying embedded sensors 720-1. More specifically, watch 700 includes an embedded sensor 720-1 (e.g., sensor unit 300 or 600) embedded into a reverse surface 730 of the watch. The reverse surface 730 of the watch is the surface of the watch against the skin of the user. FIG. 7B illustrates a possible location on a body where the wearable device of FIG. 7A might be used. In this case, the watch 700 is designed and the embedded sensors 720-1 are placed such that the embedded sensors 720-1 cover and preferably align to some extent with the radial artery 740. When a person places his or her finger tips onto the radial arteries, the person can feel his or her own heart rate and cardiac rhythm. A pulse wave sensor can measure not only heart rate and cardiac rhythm but also pulse waves which are indicative of further detailed heart health.

Figure 7C:
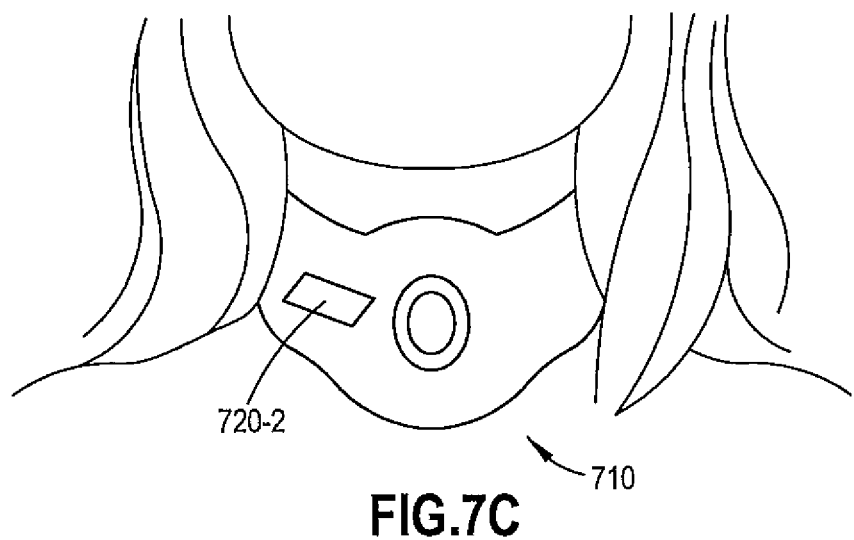
FIG. 7C illustrates another possible wearable device for carrying embedded sensors.
Figure 7D:
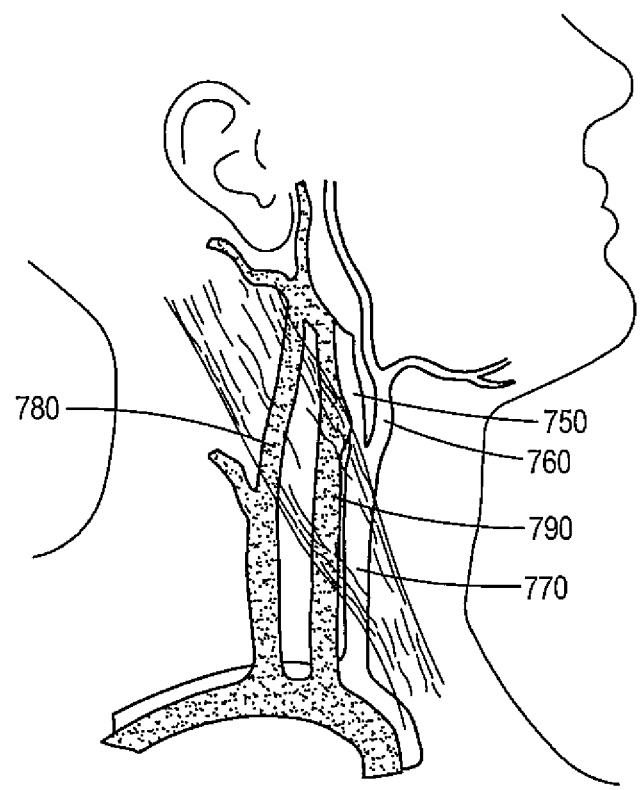
FIG. 7D illustrates another possible location on a body where the wearable device of FIG. 7C might be used.

FIG. 7C also illustrates a wearable device 710 used around the neck that has embedded sensors 720-2 in the device. The embedded sensor 720-2 is on the side of the wearable device 710 that is against the skin over jugular veins or carotid arteries, as illustrated by FIG. 7D. FIG. 7D illustrates another possible location on a body where the wearable device of FIG. 7C might be used. In this case, the wearable device 710 is designed and the embedded sensors 720-2 are placed such that the embedded sensors 720-1 cover and preferably align to some extent with one or more of the internal carotid artery 750, the external carotid artery 760, the external jugular vein 780, the internal jugular vein 790, and/or the common carotid artery. For reference, the sternocleidomastoid muscle is also shown. Deoxygenated blood flows through jugular veins from head to heart. A jugular pulse wave can show certain heart problems.

Figure 8:
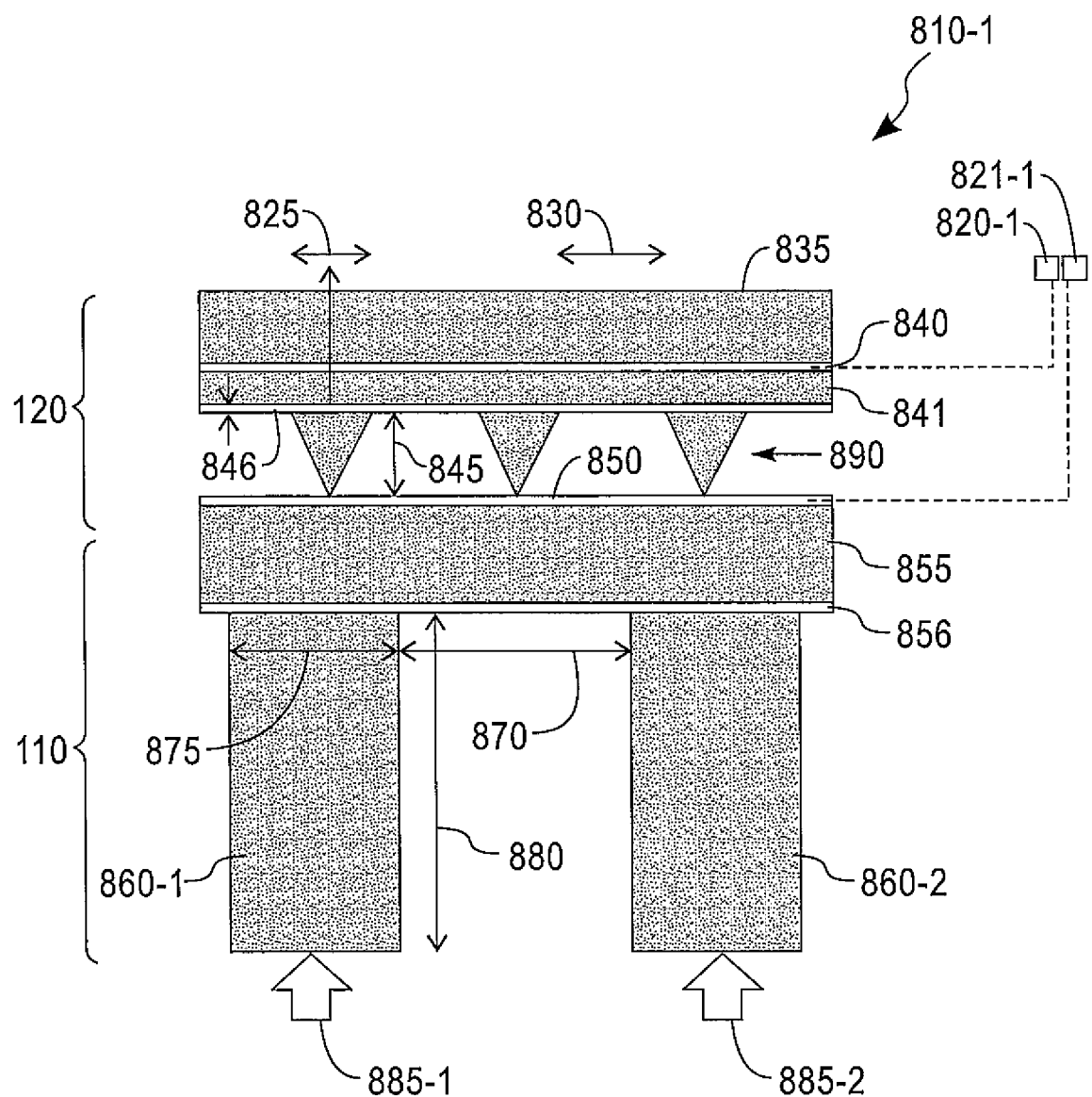
FIG. 8 is a possible example of a cross section of a layered and multi-sectional pulse wave sensor structure.

Referring to FIG. 8, FIG. 8 is a possible example of a pixel 810-1 in a layered and multi-sectional pulse wave sensor. FIG. 3 and other previous figures are also referred to for the description of FIG. 8. In particular, the pixel 810-1 is an individual pulse wave sensor unit similar to the individual pulse wave sensor unit 300 of FIG. 3. A comparison of the structure of FIG. 8 is made with the structure in FIG. 3. In this example, the sensing unit (e.g., pixel) 810-1 includes a polymer film 835 (e.g., a dielectric 335), a Cr/Au/Cr layer 840 (e.g., conductive layer 340), an adhesive layer 841, PDMS pyramids 890 (e.g., dielectric pyramids 330-1), a Cr/Au layer 850 (e.g., conductive layer 345), a polymer film 855 (e.g., a dielectric 350), an adhesive layer 856, and PDMS microhairs 860-1 and 860-2. Pixel 810-1 is connected to contacts 820-1 and 821-1. The conductive layer 840 comprises Cr/Au/Cr. Cr promotes the adhesion to the polymer film 835 and to the adhesive layer 841. Instead of Cr other metals such as Ti and TiW can be used. The wiring pads 820-1 and 821-1 have only Cr/Au as the surface of Au is bonded to another metal for electrical connection. The PDMS microhairs 860-1 and 860-2 are operated on by the pulse pressures 885-1 and 885-2, respectively. This causes a corresponding squeezing of the portion 110 and part of 120 (e.g., the layer 850 and pyramids 890), as the film 835 is assumed to be fixed, e.g., to a watch or neckband or other wearable, and there is a corresponding capacitance change. Additionally, there is a capacitance change in response to a return of the portion 110 (e.g., and part of portion 120) to an original state. In this example, the pyramid base's width 825 is 10 µm, the distance 830 between edges of pyramids is 20 µm, distance 845 between a surface of a thin layer 846 of PDMS and a surface of the Cr/Au layer 850 is 7-8 µm, distance 870 between the PDMS microhairs 860 is 60-120 µm, hair length 880 of the PDMS microhairs 860 is 150-450 µm, and diameter 875 (e.g., assuming the microhairs are cylindrical) of the PDMS microhairs 860 is 20-50 µm. The adhesive layers can be made from a Phenoxy resin with a low molecular weight. See the InChem Corp online brochure on www.phenoxy.com. Furthermore, the elastomeric polymer (e.g., as used in the pyramids 890) may comprise polydimethylsiloxane, the flexible polymer film (e.g., as used in the polymer film 855) may comprise polyester, polyimide, polyethylene, polypropylene, polycarbonate, polyvinyl chloride, acrylic polymer, fluorinated polymer, polyethylene naphthalene or combination of two or more of these polymers, and the adhesive may comprise Phenoxy resins or polyvinyl alcohol.

Figure 9:
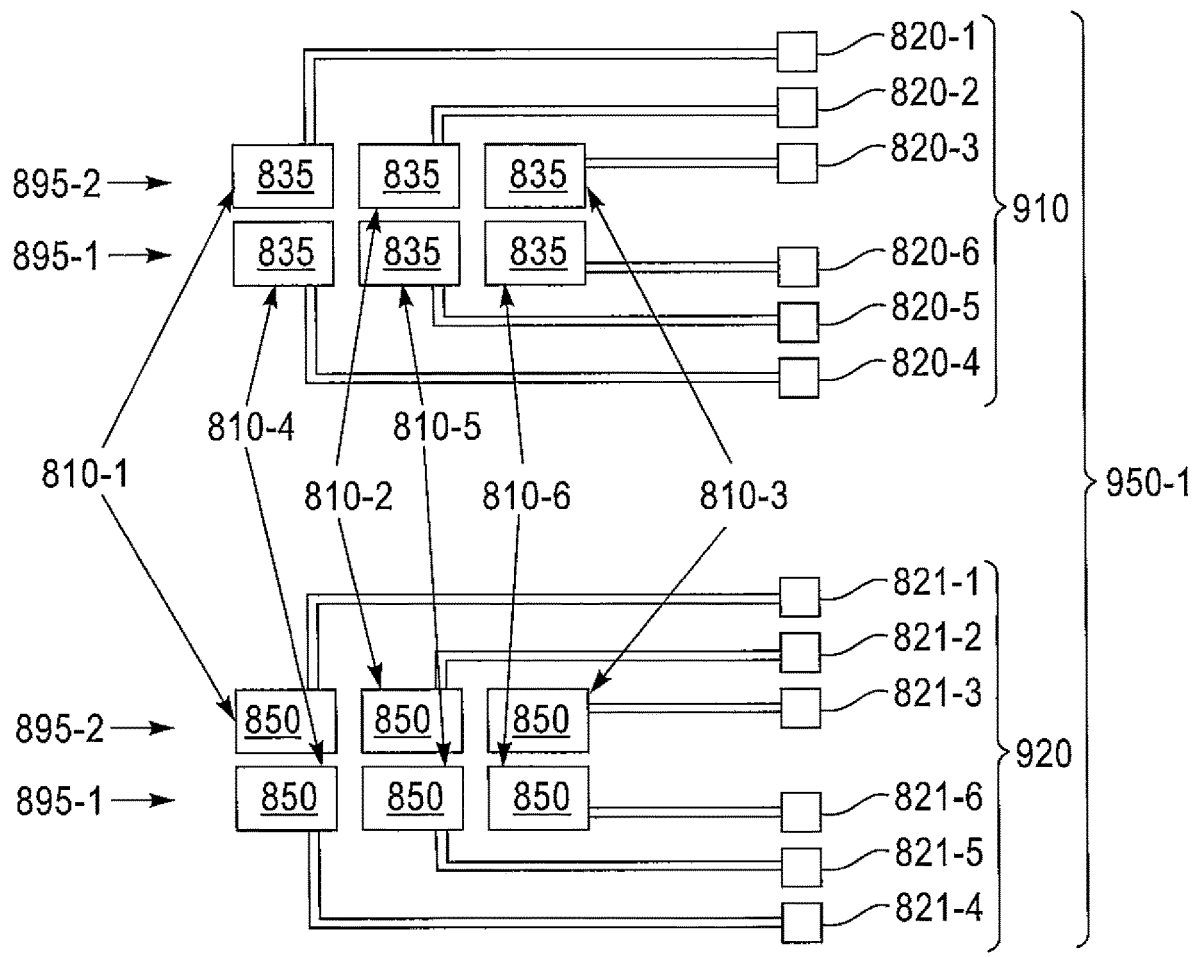
FIG. 9 illustrates one possible example configuration for the electrodes of a layered and multi-sectional pulse wave sensor structure.

FIG. 9 illustrates one possible example configuration for a layered and multi-sectional pulse wave sensor structure 950-1. The single-layered and multi-sectional pulse wave sensor structure 950-1 has two electrodes 910 and 920, each of which includes six sections, which are pixels 810-1 through 810-6. The electrode 910 would be mated with the electrode 920 in order to create the layered and multi-sectional pulse wave sensor structure 950-1. Each of the pixels is an individual sensor unit and has a structure such as the sensor units shown in FIG. 3, 6, or 8, although for ease of description the pixels 810 in FIG. 8 are used. Each pixel 810 is an individual sensor that is connected to two contacts (e.g., pads) 820 and 821, which are used for input and output pixel 810-1 is connected to contacts 820-1 and 821-1; pixel 810-2 is connected to contacts 820-2 and 821-2; pixel 810-3 is connected to contacts 820-3 and 821-3; pixel 810-4 is connected to contacts 820-4 and 821-4; pixel 810-5 is connected to contacts 820-5 and 821-5; and pixel 810-6 is connected to contacts 820-6 and 821-6. Each pixel 810 is individual in that it produces an individual waveform that captures capacitance modifications and is individually accessible.

There are two adjacent rows 895-1, 895-2 of individual sensor units, although a single row may be used (e.g., as illustrated by FIG. 2). In this example, each pixel 810 in one row 895 is aligned with a pixel 810 in another row 895, but this is not strictly necessary. Two rows 895 are used in an example in order to enhance the chance of placing either row in a wearable device along an artery. The number of rows may be increased (e.g., to three or four or more), or only one row 895 may be used. The pixels 810-1/810-4 may be section I 130 (see FIG. 2) (e.g., closest to the hand); pixels 810-2/810-5 may be section II 140 (e.g., a middle section); and pixels 810-3/810-6 may be section III 150 (e.g., towards the inner arm). As examples, each pixel 810 could be 5 mm×2.5 mm, 10 mm×5 mm, 10 mm×10 mm or 30 mm×10 mm. It is further noted that the width of a sensor (e.g., a pixel 810) is typically larger than the diameter of an artery of measurement so that a small movement of the wearable device would not cause misplacement. It is also noted that three pixels in one row can be combined into one large pixel.

Figure 10:
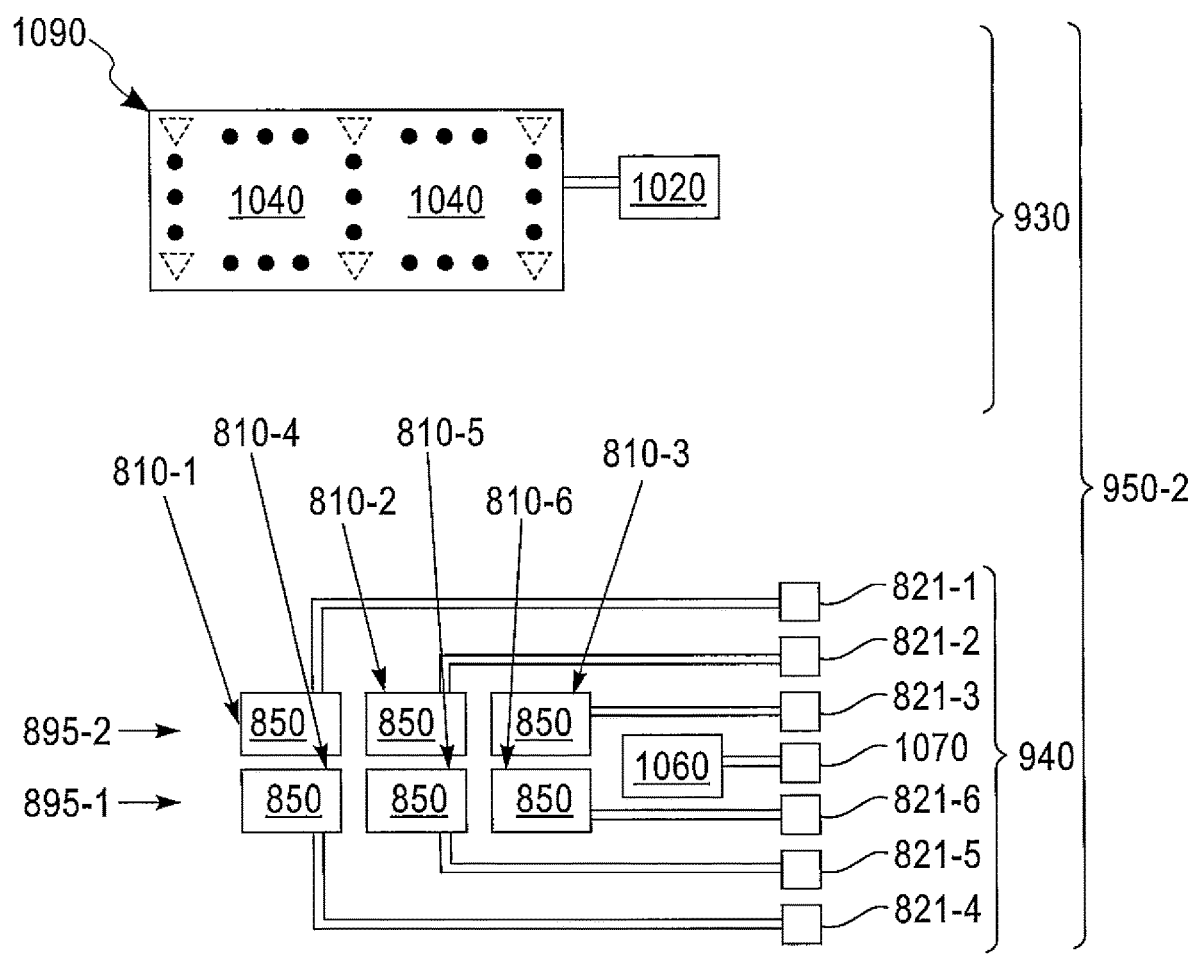
FIG. 10 is another possible example configuration for a layered and multi-sectional pulse wave sensor and uses parts of the structures in FIGS. 8 and 9.

Turning to FIG. 10, this figure illustrates another possible example configuration for a single-layered and multi-sectional pulse wave sensor structure 950-2 and uses parts of the structures in FIGS. 8 and 9. The structure 950-2 includes two electrodes 930 and 940. The electrode 940 is similar to the electrode 920 of FIG. 9, except that the electrode 940 includes one contact 1070 and a contact 1060. In this example, the six pixels 810 are still used. However, instead of a Cr/Au/Cr layer 840 for each pixel 810, in the electrode 930 there is one large Cr/Au/Cr layer 1040 that overlies all of the pixels 810 and their corresponding Cr/Au layers 850. The pad 1020 is used to contact this large Cr/Au/Cr layer 1040 and electrically connect to the contact 1060 (e.g., possibly using conductive adhesive). The wiring pads 1020, 1060 and 1070 comprise Cr/Au and the Au surface will be electrically connected to another metal in a sensor assembly process. In FIGS. 8 and 9, the PDMS pyramids 890 are per pixel 810. In FIG. 10, however, there is a large set of PDMS pyramids 1090, which cover all of the pixels 810 and the large Cr/Au/Cr layer 1040. The pyramids 1090 are shown as being dashed, since they are "under" the layer 1040 in this example. Note that it is possible for the set of PDMS pyramids 1090 to extend about 1 mm or more outside the perimeter of the large Cr/Au/Cr layer 1040, as this helps when building a layered and multi-sectional pulse wave sensor structure 950, as this makes it easier to align the large Cr/Au/Cr layer 1040 to the set of PDMS pyramids 1090. This technique may also be used per pixel 810 in FIG. 8. However, this technique is not necessary. In the example of the sensor stricture of FIG. 10, there are still six outputs from the pixels 810, which can be used to determine waveforms modified by changing capacitance. It is further noted that the layer 1040 can be divided into two and that three pixels in 895-1 or 895-2 can be combined into one large pixel.

Regarding the embodiments herein that use pyramids as one possible dielectric layer in the sensing portion of the sensors, we learned that the sensitivity of the elastomeric pyramid-containing sensors depends on the density of the pyramids in a unit area. The density of pyramids can be decreased by increasing the distances among pyramids. But if the distance is increased too much, the electrode can collapse due to lack of the physical supports by the pyramids. In an example, if the base width of a pyramid is 10 µm, the distance between the bases of the two neighboring pyramids can be from 10 µm to 1000 µm. The polymer film 835 in FIG. 8 (for instance) can be flexible for a relatively high density such as a 10-um distance and stiffer for the low density such as a 1000-um distance. It is important to applications to decrease the pyramid population by increasing the distance among neighboring pyramids. It is further noted that elastomeric pyramids are made using an elastomer solution such as PDMS and a mold such as silicon 100. For example, a silicon (100) wafer is etched with a potassium hydroxide (KOH) solution to yield reverse pyramid pits. Then a solution of PDMS is spin-coated onto the etched silicon wafer mold followed by curing the PDMS. The cured solid PDMS is pulled out of the silicon wafer mold to get the PDMS pyramids. The pyramid side-wall angle of 54.7 degree forms when the silicon is etched with KOH due to the different etch rates in the different silicon crystallographic planes in KOH.

Figure 11:
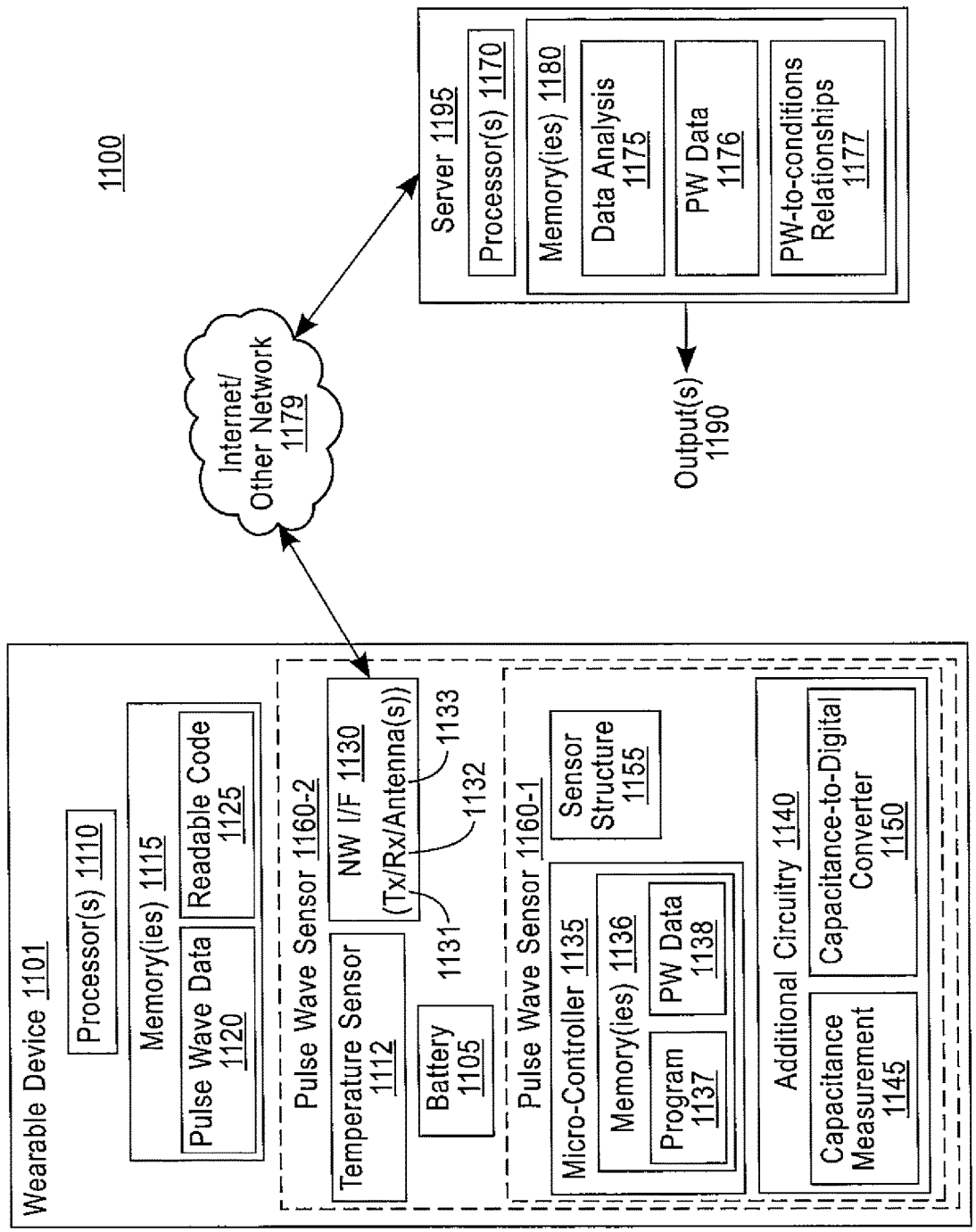
FIG. 11 is an example of a system for using layered and multi-sectional pulse wave sensors and the data therefrom, in accordance with certain exemplary embodiments.

Referring to FIG. 11, this figure is an example of a system 1100 for using layered and multi-sectional pulse wave sensors 1160 and the data therefrom, in accordance with certain exemplary embodiments. The system 1100 comprises a wearable device 1101 that includes, in one example, one or more processor(s) 1110, a battery 1105, a network (NW) interface (I/F) 1130, one or more memories 1115, a temperature sensor 1112, and a layered and multi-sectional pulse wave sensor 1160. The network interface 1130 includes a transmitter (Tx) 1131, a receiver (Rx) 1132, and one or more antennas 1133. The one or more memories include pulse wave data 1120 and computer readable code 1125. In an exemplary embodiment, the one or more processors 1110 execute the computer readable code 1125 and cause the wearable device to perform operations as described herein. In another example, the operations are embedded into the one or more processors 1110 (or other circuitry), e.g., as hardware elements, and the one or more processors 1110 perform the operations. In a further example, some combination of hardware or code may be used to implement the operations described herein.

The layered and multi-sectional pulse wave sensor 1160-1 comprises a micro-controller 1135, a sensor structure 1155, and additional circuitry 1140. The micro-controller 1135 comprises one or more memories 1136, which comprise a program 1137 of computer readable code and pulse wave data 1138. The additional circuitry 1140 comprises capacitance measurement circuitry 1145 and capacitance-to-digital converter circuitry 1150.

The sensor structure 1155 includes multiple sections, such as three or six sections (see FIG. 8), each section being an individual sensor unit (also called a pixel). Each pixel 810 may include its own conductive layer 840 (see FIGS. 8 and 9) or the set of pixels 810 may have a single conductive layer 1040 (see FIG. 10). The structures may be as in FIG. 3, 6, or 9.

The micro-controller 1135 can execute code in the program 1137 to cause the pulse wave sensor 1160-1 to perform operations described herein, or the operations can be embedded as hardware (e.g., in the micro-controller 1135 or other device), or some combination of these may be used. The micro-controller 1135 can cause the capacitance measurement circuitry 1145 to determine waveforms, for all of the individual sensing units, capturing changes in capacitance in the sensor structure 1155 caused in response to bending of the first and second layers by a pulse wave under the skin. The waveforms are converted to digital by the capacitance-to-digital converter 1150 and stored as PW data 1138 in the one or more memories 1136.

The one or more processors 1110 can cause the pulse wave sensor 1160-1 to transfer the PW data 1138 to the one or more processors 1110, which then stores the data in the memory/memories 1115 as pulse wave data 1120. The one or more processors 1110 can cause the wearable device 1101, using the network interface 1130, to transmit the pulse wave data 1120 to the server 1195 via the wireless network interface 1130.

In another example, the wearable device 1101 does not include the one or more processors 1110 or the one or more memories 1115, and "only" includes the pulse wave sensor 1160-2. Pulse wave sensor 1160-2 includes the battery 1105 and the network interface 1130 and transmits the PW data 1138 to the server 1195.

In this example, the pulse wave data 1120 is transmitted to a server 1196 via a wired or wireless (or both) network such as the Internet 1179. The server 1195 comprises one or more processors 1170 and one or more memories 1180, which comprise a data analysis program 1175 of computer readable code. The one or more processors 1170, in response to execution of the computer readable code in the data analysis program 1175, cause the server to perform data analysis of the pulse wave data 1176, which are one or more versions of the pulse wave data 1120/1138.

The digitized data from the pulse wave data 1176 may be analyzed and correlated with specific heart problems, and the subsequent relationships may be used to diagnose patients. The digitized data from the pulse wave data 1176 may be correlated with other than heart problems, and the subsequent relationships are used to diagnose patients. The digitized data from the pulse wave data 1176 may be correlated with organ health status, and the subsequent relationships are used to diagnose the health status of patients. These relationships 1177 may be stored in the server 1195, which may use them as early warning system. For instance, the server 1195 can create output(s) 1190, which can be sent to the person using the wearable device 1101, a doctor, or other healthcare professional or entity (such as a hospital). The output(s) could indicate the conditions (e.g., heart problems, other than heart problems, health status including good or poor health status or no change from previous outputs, and the like).

Although the computer system 1195 is characterized as a "server", this is only one possibility. The computer system 1195 may also be "local" to the person using the wearable device 1101, such as being an app on the person's smartphone, tablet, or computer system. In this case, the network 1179 could be a local wireless (e.g., Wi-Fi) or wired network. Furthermore, the "server" and the wearable device 1101 can be combined into one device, as the processing performed by the server 1195 could be performed, e.g., by an app on a watch for instance. The pulse wave data 1120/1138 may be stored locally (e.g., by the person using the wearable device 1101) or remotely such as in the "cloud".

The processors 1110, 1135, and 1170 may be any suitable processing device for the particular environment, such as application specific integrated circuits, single or multicore processors, low power processors (e.g., as used in smartphones or tablets), general purpose processors, and the like. The memories may be any suitable memory, such as RAM, ROM, removable memory, memories internal or external to processors, memory that retains its values without power or only retains its values with power, and the like.

Portions of the data collection and a compression algorithm may also be carried out in the program running on the microcontroller 1135 making the capacitance to digital measurements. This program could be in an assembly code. This would reduce the amount of data that would need to be transmitted (e.g., wirelessly) to the server which would in turn lower the power consumption (an advantage for battery power operation). In the simplest example, the microcontroller 1135 would know enough not to transmit when no pulse is detected (e.g., not attached to the patient yet), as opposed to continually transmitting capacitance to digital results. The microcontroller could place the sensor 1160-1 into an off state (e.g., where no measurements are made and, e.g., no current is passed into the capacitor(s)) in response to no pulse being detected. In addition, the microcontroller 1135 could cause the sensor 1160-1 to perform measurements only periodically even if a pulse is detected. Additionally, a temperature sensor 1112 could be included and the microcontroller could use data from the temperature sensor 1112 (e.g., configured to sense temperature from the skin) to determine whether to take sensor data or not. For instance, if the temperature reading from the temperature sensor 1112 does not meet some criterion (e.g., within a few degrees of normal body temperature for a human or animal), the microcontroller could place the sensor 1160-1 into an off state (e.g., where no measurements are made and, e.g., no current is passed into the capacitor(s)).

Figure 12A:
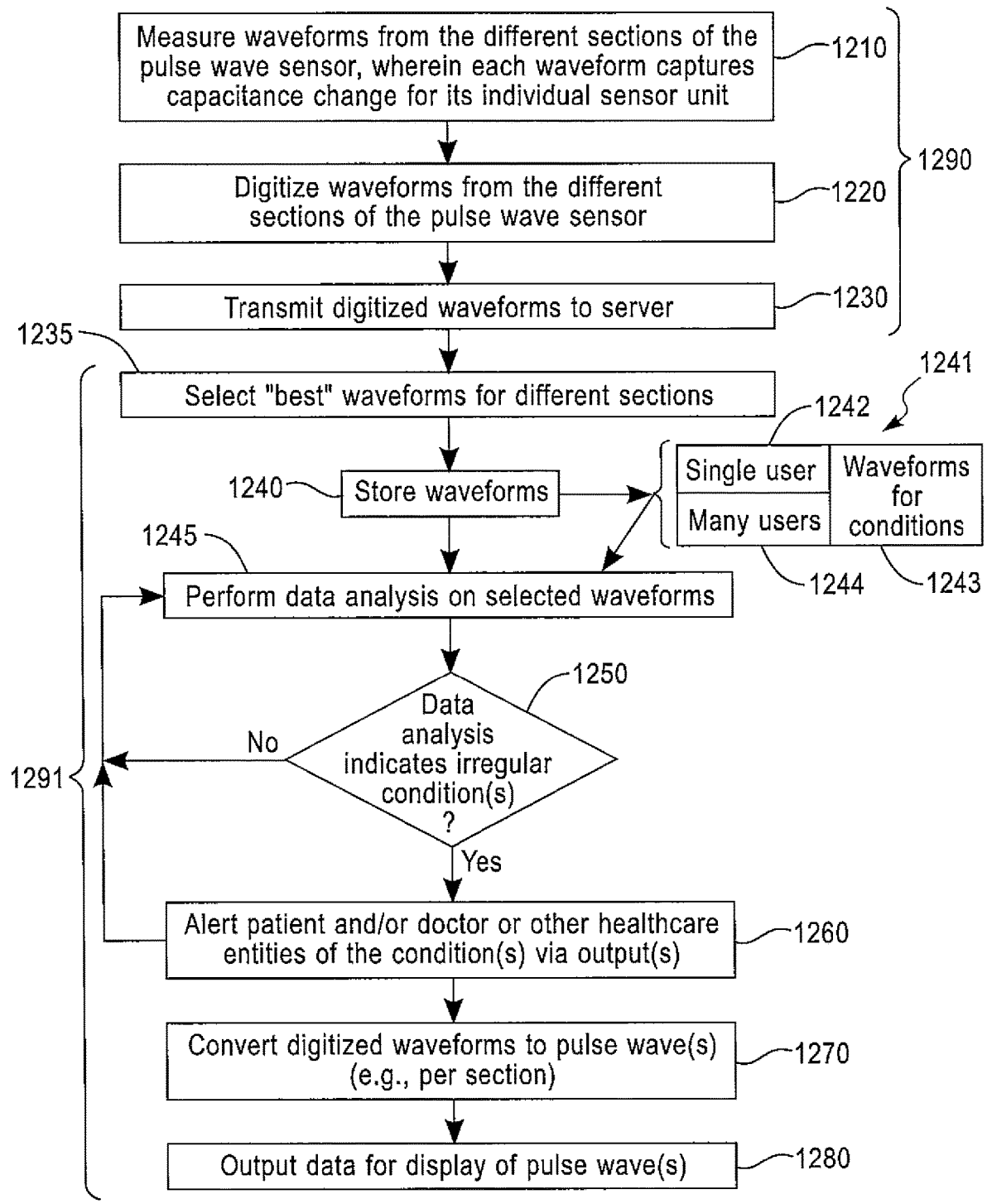
FIGS. 12A and 12B, collectively referred to herein as FIG. 12, illustrate a logic flow diagram for using information from layered and multi-sectional pulse wave sensors in an exemplary embodiment, and illustrate the operation of an exemplary method, a result of execution of computer program instructions embodied on a computer readable memory, functions performed by logic implemented in hardware, and/or interconnected means for performing functions in accordance with an exemplary embodiment.
Figure 12B:
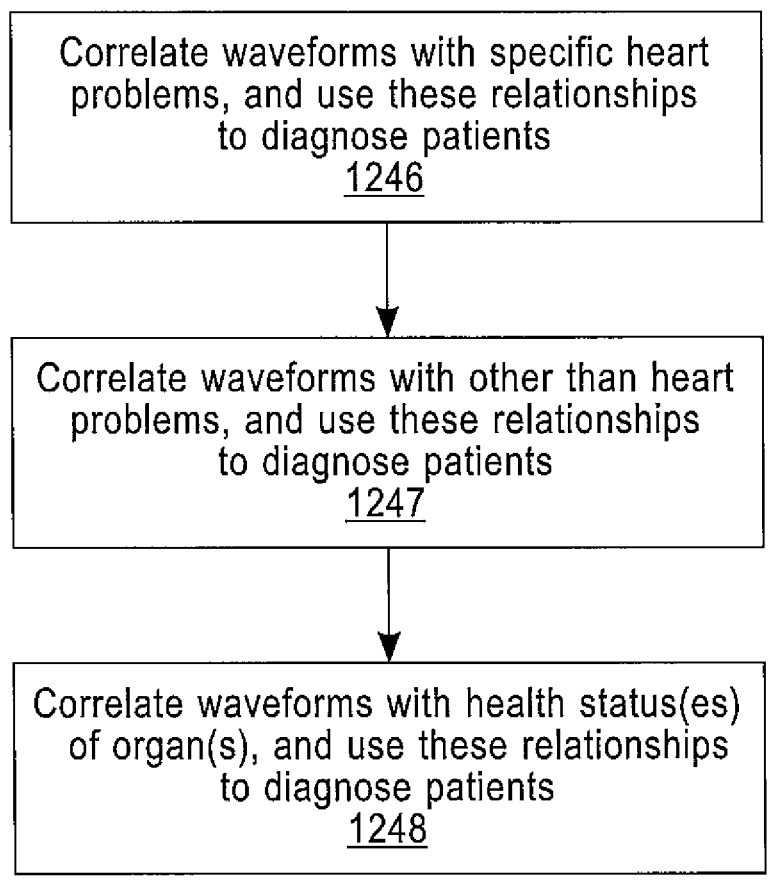

Turning to FIGS. 12A and 12B, collectively referred to herein as FIG. 12, these figures illustrate a logic flow diagram for using information from layered and multi-sectional pulse wave sensors in an exemplary embodiment. These figures also illustrate the operation of an exemplary method, a result of execution of computer program instructions embodied on a computer readable memory, functions performed by logic implemented in hardware, and/or interconnected means for performing functions in accordance with an exemplary embodiment. In particular, the blocks may be means for performing the associated functions.

In FIG. 12, reference 1290 indicates blocks that are performed by a layered and multi-sectional pulse wave sensor 1160, and reference 1291 indicates blocks that are performed by a computer system such as server 1195. This example uses the layered and multi-sectional pulse wave sensor 1160-1 of FIG. 11, and uses a server 1195 (e.g., instead of a local computer system such as a smartphone). As indicated above, this is merely exemplary, and all blocks may, e.g., be performed by one device.

In block 1210, the sensor 1160 measures (e.g., using the capacitance measurement circuitry 1145) waveforms from the different sections of the pulse wave sensor 1160. In this case, each section corresponds to an individual sensor unit 810. Each waveform captures capacitance change for its individual sensor unit 810. Specifically, the first and second portions 110, 120 are configured to create a capacitance change in response to a squeezing between the first portion 110 and a fixed part of the second portion 120 caused by a pulse pressure under the skin and in response to a return to an original state of the first portion with a release of the pulse pressure. In block 1220, the sensor 1160 digitizes (e.g., using the capacitance-to-digital converter 1150) waveforms from the different sections of the pulse wave sensor. In block 1230, the sensor 1160 transmits the digitized waveforms to the server 1195.

In certain examples herein (see FIG. 8), six or more pixels may be used, and also two or more sections 130, 140, 150 may be used. Each group of two pixels, in the example of FIG. 8, is used for one of the sections 130, 140, and 150. It is expected that a detection of pulse by each pixel will be different due to a difference of contact. For these examples, the "best" digitized waveform (e.g., in each group 810-1/810-4, 810-2/810-5, 810-3/810-6) can be chosen for diagnosis. See block 1235. The "best" digitized waveform may be chosen using a number of criterion/criteria, such as the most sensitive and/or the most accurate. It is noted that block 1235 may not be used, e.g., if there is one row 895 of pixels 810 or if multiple pixels are employed to diagnose multiple organs simultaneously.

In block 1240, the server 1195 stores the digitized waveforms, e.g., for a single user 1242 or for many users 1244, in a database 1241. The stored waveforms for the single user 1242 may be used, e.g., to determine any deviation from previous waveforms. Note that only a representative sample may be stored if desired. The stored waveforms for many users 1244 may be used to determine waveforms for certain conditions 1243. For instance, after many waveforms for many users 1244 have been stored and analyzed, waveforms associated with heart attacks (myocardial infarctions) may be determined and representative versions of these stored in 1243. The current waveforms may be compared with the waveforms for the heart attack 1243, and such a comparison can determine whether a heart attack has occurred.

In block 1245, the server 1195 performs data analysis on the (selected) waveforms. In block 1250, the server determines whether the data analysis indicates an irregular condition (or more than one irregular condition). If no irregular conditions are determined (block 1250=No), the flow proceeds to block 1245, where the server awaits other digitized waveforms. If one or more irregular conditions are determined (block 1250=Yes), in block 1260, the server 1195 alerts (block 1260) the patient (e.g., the user of the wearable device 1101) and/or the doctor (or other healthcare entities, such as emergency services, a hospital, and the like) of the condition(s) via the output(s) 1190.

In this example, the server 1195 is assumed to convert (block 1270) digitized waveforms to pulse waves (e.g., per section), e.g., in response to a request from a user. This block may also be performed by the layered and multi-sectional pulse wave sensor 1160 or other device. In block 1280, the server 1195 outputs data for display of pulse wave(s). For instance, the server 1195 could output data suitable for use by a webpage. These blocks 1270 and 1280 may be performed by other devices, too, such as by smartphone, tablet, or computer running an application ("app").

This example of FIG. 12 only uses irregular conditions in order to send output(s) 1190. However, the server 1195 can also send outputs for normal conditions. For instance an output having the meaning of "your pulse wave is normal" could be sent.

In FIG. 12B, different possibilities are shown for block 1245, where the server 1195 performs data analysis on the (selected) pulse waves.

One possibility for data analysis is illustrated by block 1246, where the server 1195 correlates waveforms with specific heart problems, and uses these relationships to diagnose patients. Another possibility occurs for block 1247, where the server 1195 correlates the waveforms with other than heart problems such as lung, stomach, liver, etc. as described above, and uses these relationships to diagnose patients. Block 1248 illustrates a further possibility, where the server 1195 correlates the waveforms with health status (es) of organ(s), and uses these relationships to diagnose patients.

Figure 13:
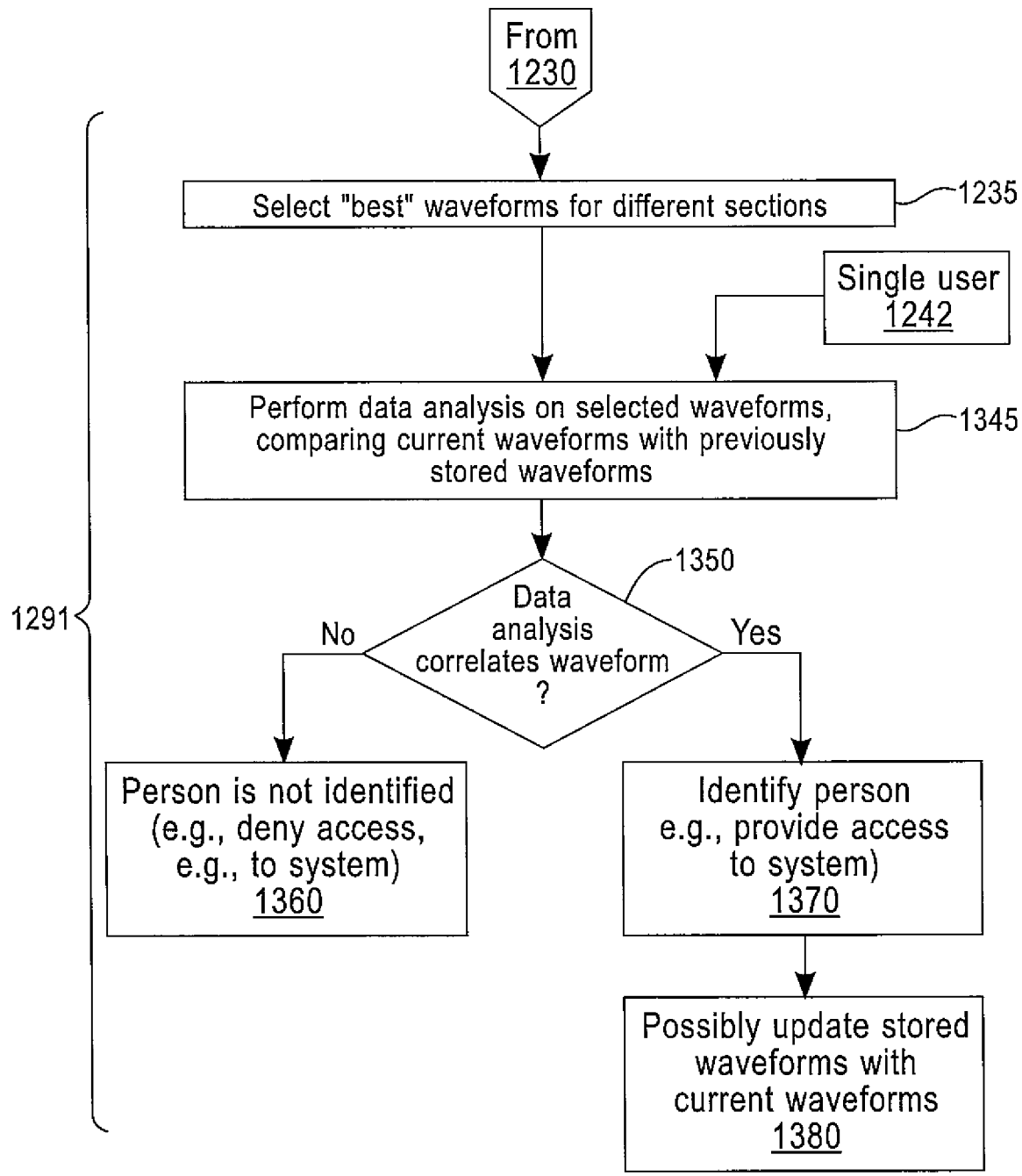
FIG. 13 illustrates a logic flow diagram for using information from layered and multi-sectional pulse wave sensors in an exemplary embodiment, and illustrates the operation of an exemplary method, a result of execution of computer program instructions embodied on a computer readable memory, functions performed by logic implemented in hardware, and/or interconnected means for performing functions in accordance with an exemplary embodiment.

Referring to FIG. 13, this figure illustrates a logic flow diagram for using information from layered and multi-sectional pulse wave sensors in an exemplary embodiment. This figure also illustrates the operation of an exemplary method, a result of execution of computer program instructions embodied on a computer readable memory, functions performed by logic implemented in hardware, and/or interconnected means for performing functions in accordance with an exemplary embodiment. In particular, the blocks may be means for performing the associated functions.

FIG. 13 is assumed to be performed by the server 1291, e.g., under control of the data analysis program 1175, but may be performed by other computer systems such as a tablet or watch. Block 1235 is reached from block 1230 of FIG. 12A in this example, and block 1235 is the same as in FIG. 12A. In block 1345, the server performs data analysis on selected waveforms, comparing current waveforms with previously stored waveforms from block 1242. If the data analysis correlates the waveforms (block 1350=Yes), the person is identified (block 1370). This application can be useful in such areas, e.g., as banking security or other areas requiring identification of an individual. The person may therefore be granted access to a system such as a banking system (block 1370). Additionally, in block 1380, the server may possibly update the stored with the current waveforms. In contrast, if the data analysis does not correlate the waveforms (block 1350=No), the person is not identified (block 1360). The person may therefore be denied access to a system such as a banking system (block 1360).

It is noted that the sensors herein may also be used for animals such as dogs, cats, or horses. The term "skin" therefore can encompass skin for these animals. The sensor may have to be changed, e.g., to make a good contact of a sensor with an animal pulse, although a contact area could be cleared of hair, too.

As will be appreciated by one skilled in the art, aspects of the present invention may be embodied as a system, method or computer program product. Accordingly, aspects of the present invention may take the form of an entirely hardware embodiment, an entirely software embodiment (including firmware, resident software, micro-code, etc.) or an embodiment combining software and hardware aspects that may all generally be referred to herein as a "circuit," "module" or "system." Furthermore, aspects of the present invention may take the form of a computer program product embodied in one or more computer readable medium(s) having computer readable program code embodied thereon.

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device. A computer readable storage medium does not include a propagating wave.

A computer readable signal medium may include a propagated data signal with computer readable program code embodied therein, for example, in baseband or as part of a carrier wave. Such a propagated signal may take any of a variety of forms, including, but not limited to, electromagnetic, optical, or any suitable combination thereof. A computer readable signal medium may be any computer readable medium that is not a computer readable storage medium and that can communicate, propagate, or transport a program for use by or in connection with an instruction execution system, apparatus, or device.

Program code embodied on a computer readable medium may be transmitted using any appropriate medium, including but not limited to wireless, wireline, optical fiber cable, RF, etc., or any suitable combination of the foregoing.

Computer program code for carrying out operations for aspects of the present invention may be written in any combination of one or more programming languages, including an object oriented programming language such as Java, Smalltalk, C++ or the like and conventional procedural programming languages, such as the "C" programming language or similar programming languages. The program code may execute entirely on the designer's computer, partly on the designer's computer, as a stand-alone software package, partly on the designer's computer and partly on a remote computer or entirely on the remote computer or server. In the latter scenario, the remote computer may be connected to the designer's computer through any type of network, including a local area network (LAN) or a wide area network (WAN), or the connection may be made to an external computer (for example, through the Internet using an Internet Service Provider).

Aspects of the present invention are described above with reference to flowchart illustrations and/or block diagrams of methods, apparatus (systems) and computer program products according to embodiments of the invention. It will be understood that each block of the flowchart illustrations and/or block diagrams, and combinations of blocks in the flowchart illustrations and/or block diagrams, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks.

These computer program instructions may also be stored in a computer readable medium that can direct a computer, other programmable data processing apparatus, or other devices to function in a particular manner, such that the instructions stored in the computer readable medium produce an article of manufacture including instructions which implement the function/act specified in the flowchart and/or block diagram block or blocks.

The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified in the flowchart and/or block diagram block or blocks.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The following abbreviations that may be found in the specification and/or the drawing figures are defined as follows:
AC alternating current
AP augmentation period
CVDs cardiovascular diseases
DBP diastolic blood pressure
DC direct current
EKG electrocardiogram
FET field effect transistor
I/F interface
IP inflection point
IT information technology
JVPs jugular venous pulses
NW network
PDMS polydimethylsiloxane
PP pulse pressure
Rx receiver
SAMs self-assembled monolayers
SBP systolic blood pressure
Tx transmitter
WHMS wearable health-monitoring systems
WHO world health organization

What is claimed is:

1. A computer-implemented method, comprising:
accessing data comprising previously measured and stored waveforms for individual sensors having a corresponding plurality of individual sensor units placed in a row and responsive to pulse pressure under skin for corresponding ones of one or more people,
wherein each previously measured waveform captures capacitance change caused by the pulse pressure for its corresponding individual sensor unit from a corresponding sensor,
selecting a waveform from the stored single waveforms;
comparing the selected waveform with the stored waveforms of the data;
diagnosing at least one irregular condition based on the comparison; and
outputting an indication of the diagnosis to a healthcare entity indicating the at least one irregular condition for a person, from the one or more people, corresponding to the selected waveform,
wherein each of the individual sensors comprises:
a sensor structure, comprising:
the plurality of the individual sensor units placed in the row, each individual sensor unit comprising:
a first portion configured to contact a surface of the skin under which arteries or veins or both are to be located; and
a second portion that contacts the first portion and is configured to have a capacitance, wherein the first and second portions are configured to create a capacitance change in response to a squeezing or bending between the first portion and a fixed part of the second portion caused by a pulse pressure under the skin and in response to a return to an original state of the first portion with a release of the pulse pressure;
circuitry connected to the sensor structure and configured to measure waveforms for the plurality of individual sensor units and configured to digitize the measured waveforms, wherein each measured waveform captures the capacitance change for its corresponding individual sensor unit;
a wireless interface, the wireless interface configured to transmit the digitized measured waveforms,
wherein the previously measured waveforms are based on the digitized measured waveforms, and
wherein, for each sensor unit, the first portion comprises a plurality of microhairs and a first dielectric layer connected to the plurality of microhairs, and the second portion comprises a plurality of elastomeric dielectric pyramids having bases and apexes and a second dielectric layer connecting the bases of the pyramids, a first conductive layer contacting the first dielectric layer of the first portion and contacting the apexes of the pyramids, and a second conductive layer contacting the second dielectric layer that connects the bases of the pyramids.

2. The method of claim 1, wherein the at least one irregular condition comprises a specific heart problem.

3. The method of claim 1, wherein the at least one irregular condition comprises an irregular condition other than a heart problem.

4. The method of claim 1, wherein the at least one irregular condition comprises organ health status.

5. The method of claim 1, wherein the previously measured and stored data are from multiple people.

6. The method of claim 5, wherein the outputting further comprises alerting one or more of the person or one or more doctors about the correlation of the at least one irregular condition for the person.

7. The method of claim 1, wherein the healthcare entity comprises a doctor.

\* \* \* \* \*